US010253059B2

(12) United States Patent
Leffler et al.

(10) Patent No.: US 10,253,059 B2
(45) Date of Patent: Apr. 9, 2019

(54) HYBRID GALACTOSIDE INHIBITOR OF GALECTINS

(71) Applicant: GALECTO BIOTECH AB, Copenhagen (DK)

(72) Inventors: Hakon Leffler, Lund (SE); Ulf Nilsson, Lund (SE); Fredrik Zetterberg, Askim (SE)

(73) Assignee: GALECTO BIOTECH AB, Copenhagen (DK)

( * ) Notice: Subject to any disclaimer, the term of this patent is extended or adjusted under 35 U.S.C. 154(b) by 143 days.

(21) Appl. No.: 15/323,967

(22) PCT Filed: Jul. 6, 2015

(86) PCT No.: PCT/EP2015/065313
§ 371 (c)(1),
(2) Date: Jan. 5, 2017

(87) PCT Pub. No.: WO2016/005311
PCT Pub. Date: Jan. 14, 2016

(65) Prior Publication Data
US 2017/0349622 A1 Dec. 7, 2017

(30) Foreign Application Priority Data

Jul. 9, 2014 (EP) .................................... 14176421
Jul. 18, 2014 (EP) .................................... 14177599

(51) Int. Cl.
C07H 19/056 (2006.01)
C07H 13/04 (2006.01)
C07H 13/08 (2006.01)
C07H 15/26 (2006.01)

(52) U.S. Cl.
CPC ........... C07H 19/056 (2013.01); C07H 13/04 (2013.01); C07H 13/08 (2013.01); C07H 15/26 (2013.01)

(58) Field of Classification Search
None
See application file for complete search history.

(56) References Cited

U.S. PATENT DOCUMENTS

| 7,230,096 | B2 | 6/2007 | Nilsson |
| 7,638,623 | B2 | 12/2009 | Nilsson |
| 7,700,763 | B2 | 4/2010 | Leffler |
| 8,236,771 | B2 | 8/2012 | Cicciarelli |
| 8,697,862 | B2 | 4/2014 | Nilsson |
| 8,703,720 | B2 | 4/2014 | Leffler |
| 9,243,021 | B2 * | 1/2016 | Sethi ..................... A61M 15/00 |
| 9,353,141 | B2 * | 5/2016 | Nilsson .................. C07H 15/26 |
| 9,580,456 | B2 * | 2/2017 | Nilsson ................ A61M 15/00 |
| 9,688,713 | B2 * | 6/2017 | Sethi ..................... A61M 15/00 |
| 2004/0147730 | A1 | 7/2004 | Nilsson |
| 2007/0185039 | A1 | 8/2007 | Leffler |
| 2007/0185041 | A1 | 8/2007 | Nilsson |
| 2008/0213786 | A1 | 9/2008 | Hurez |
| 2011/0130553 | A1 | 6/2011 | Nilsson |
| 2012/0165277 | A1 | 6/2012 | Leffler |
| 2014/0011765 | A1 | 1/2014 | Nilsson |
| 2014/0099319 | A1 | 4/2014 | Traber |
| 2014/0171630 | A1 | 6/2014 | Nilsson |
| 2014/0200190 | A1 | 7/2014 | Leffler |

FOREIGN PATENT DOCUMENTS

| WO | 2005113568 | 12/2005 |
| WO | 2005113569 | 12/2005 |
| WO | 2010126435 | 11/2010 |
| WO | 2013110704 | 8/2013 |
| WO | 2014067986 | 5/2014 |
| WO | 2014078655 | 5/2014 |

OTHER PUBLICATIONS

Cumpstey et al., Chemistry—A European Journal, vol. 14(14), pp. 4233-4245, 2008.*
Rabinovich et al. (2004). Shedding light on the immunomodulatory properties of galectins: Novel regulators of innate and adaptive immune responses. Glycoconjugate J. 19:565-573.
Rojanathammanee et al. (2011). Expression of mutant alpha-synuclein modulates microglial phenotype in vitro. Journal of Neuroinflammation 8:44.
Saksida et al. (2012). Galectin-3 Deficiency Protects Pancreatic Islet Cells from Cytokine-Triggered Apoptosis in Vitro. J. Cell. Phys. 228:1568-1576.
Salameh et al. (2010). 1H-1,2,3-Triazol-1-yl thiodigalactoside derivatives as high affinity galectin-3 inhibitors. Bioorg. Med. Chem. 18: 5367-5378.
Salameh et al. (2006). Thioureido N-acetyllactosamine derivatives as potent galectin-7 and 9N inhibitors. Bioorganic and Medicinal Chemistry 14:1215-1220.
Sato et al. (2004). Seeing strangers or announcing "danger": Galectin-3 in two models of innate immunity. Glycoconjugate J. 19: 583-591.
Soomro et al. (2011). CuAAC synthesis of resorcin[4]arene-based glycoclusters as multivalent ligands of lectins. Org. Biomolec. Chem. 9:6587-6597.
Sörme et al. (2003a.) Fluorescence polarization to study galectin-ligand interactions. Meth. Enzymol. 362: 504-512.
Sörme et al. (2003b). Design and synthesis of galectin inhibitors. Meth. Enzymol. 363: 157-169.
Sörme et al. (2002). Low micromolar inhibitors of galectin-3 based on 3'-derivatization of N-acetyllactosamine. ChemBioChem 3:183-189.

(Continued)

Primary Examiner — Traviss C McIntosh, III
(74) Attorney, Agent, or Firm — Cheryl H Agris; Agris & von Natzmer, LLP

(57) ABSTRACT

The present invention relates to a compound of the general formula (1). The compound of formula (1) is suitable for use in a method for treating a disorder relating to the binding of a galectin, such as galectin-3 to a ligand in a mammal, such as a human. Furthermore the present invention concerns a method for treatment of a disorder relating to the binding of a galectin, such as galectin-3 to a ligand in a mammal, such as a human.

22 Claims, No Drawings

(56) References Cited

OTHER PUBLICATIONS

Thijssen et al. (2006). Galectin-1 is essential in tumor angiogenesis and is a target for antiangiogenesis therapy. PNAS 103:15975-15980.
Trahey et al (1999). Cyclophilin C-associated protein: A normal secreted glycoprotein that down-modulates endotoxin and proinflammatory responses in vivo. Proc. Natl. Acad. Sci. USA 96:3006-3011.
Unal-Cevik et al. (2011). Alpha-synuclein aggregation induced by brief ischemia negatively impacts neuronal survival in vivo: a study in [A30P]alpha-synuclein transgenic mouse. J. Cereb. Blood Flow and Metab.31:913-923.
Van Den Brule et al. (2004). Expression of galectins in cancer: A critical review. Glycoconjugate J. 19:459-465.
Van Hattum et al (2013). Tuning the Preference of Thiodigalactoside- and Lactosamine-Based Ligands to Galectin-3 over Galectin-1. J. Med. Chem. 56: 1350-1354.
Watt et al. (2004). The involvement of galectin-1 in skeletal muscle determination, differentiation and regeneration. Glycoconjugate J 19: 615-619.
International Preliminary Report on Patentability for PCT/EP2015/655313, dated Jan. 10, 2017.
International Search Report and Written Opinion for PCT/EP2015/655313, dated Sep. 17, 2015.
Doverhag et al. (2010). Galectin-3 contributes to neonatal hypoxic-ischemic brain injury. Neurobiology of Disease 38:36-46.
MacKinnon et al. (2013). Inhibition of galectin-3 reduces atherosclerosis in apolipoprotein E-deficient mice. Glycobiology 23: 654-663.
Mok et al. (2007). Role of galectin-3 in prion infections of the CNS. Biochem. Biophys. Res. Commun. 359:672-678.
Ahmad et al. (2002). Thermodynamic binding studies of cell surface carbohydrate epitopes to galectins-1, -3, and -7: Evidence for differential binding specificities. Can. J. Chem. 80:1096-1104.
Almkvist et al. (2004). Galectins as inflammatory mediators. Glycoconjugate J. 19: 575-581.
Almkvist et al. (2001). Lipopolysaccharide-induced gelatinase granule mobilization primes neutrophils for activation by galectin-3 and formylmethionyl-Leu-Phe. Infect. Immun. 69: 832-837.
Andre et al. (2004). Persubstituted Cyclodextrin-Based Glycoclusters as Inhibitors of Protein-Carbohydrate Recognition Using Purified Plant and Mammalian Lectins and Wild-Type and Lectin-Gene-Transfected Tumor Cells as Targets. Bioconjugate Chem. 15: 87-98.
Andre et al. (1999). Lactose-containing starburst dendrimers: influence of dendrimer generation and binding-site orientation of receptors (plant/animal lectins and immunoglobulins) on binding properties. Glycobiology 9: 1253-1261.
Barondes et al. (1994). Galectins. Structure and function of a large family of animal lectins. J. Biol. Chem. 269:20807-20810.
Bidon-Wagner et al. (2004). Human galectin-8 isoforms and cancer. Glycoconjugate J. 19:557-563.
Blois et al. (2007). A pivotal role for galectin-1 in fetomaternal tolerance. Nat Med 13: 1450-1457.
Brewer (2004). Thermodynamic binding studies of galectin-1,-3 and -7. Glycoconjugate J. 19:459-465.
Chen et al. (2012). Targeting Galectin-1 and Galectin-3 Attenuates VEGF-A-induced Angiogenesis. Mol. Biol. Cell (suppl), Abstract No. 3215.
Chiarotti et al. (2004). Galectin genes: Regulation of expression. Glycoconjugate J. 19:441-449.
Cumpstey et al. (2008). Double affinity amplification of galectin-ligand interactions through arginine-arene interactions: Synthetic, thermodynamic, and computational studies with aromatic diamido-thiodigalactosides. Chem. Eur. J. 14: 4233-4245.
Cumpstey et al. (2005). Synthesis of a phenyl thio-β-D-galactopyranoside library from 1,5-difluoro-2,4-dinitrobenzene: discovery of efficient and selective monosaccharide inhibitors of galectin-7. Org. Biomol. Chem. 3: 1922-1932.
Cumpstey et al. (2005). C2-Symmetrical thiodigalactoside bis-benzamido derivatives as high-affinity inhibitors of galectin-3: Efficient lectin inhibition through double arginine-arene interactions. Angew. Chem. Int. Ed. 44: 5110-5112.
Dam et al. (2008). Effects of clustered epitopes in multivalent ligand-receptor interactions. Biochemistry 47: 8470-8476.
David (2004). Design of a multivalent galactoside ligand for selective targeting of HPMA copolymer-doxorubicin conjugates to human colon cancer cells. European Journal of Cancer 40: 148-157.
Delacour et al. (2007). Apical Sorting by Galectin-3-Dependent Glycoprotein Clustering. Traffic 8: 379-388.
Delaine et al. (2008). Galectin-Inhibitory Thiodigalactoside Ester Derivatives Have Anti-Migratory Effects in Cultured Lung and Prostate Cancer Cells. J. Med. Chem. 51:8109-8114.
Fort et al. (2006). Screening for Galectin-3 Inhibitors from Synthetic Lacto-N-biose Libraries Using Microscale Affinity Chromatography Coupled to Mass Spectrometry. J. Org. Chem. 71: 7146-7154.
Garner et al. (2008). Galectin-glycan lattices regulate cell-surface glycoprotein organization and signalling. Biochem. Soc. Trans. 36: 1472-1477.
Gendronneau et al. (2008). Galectin-7 in the Control of Epidermal Homeostasis after Injury. Mol. Biol. Cell 19: 5541-5549.
Giguere et al (2006). Aryl O- and S-galactosides and lactosides as specific inhibitors of human galectins-1 and -3: Role of electrostatic potential at O-3. Bioorg. Med. Chem. 16:1668-1672.
Giguere et al. (2006). Carbohydrate triazoles and isoxazoles as inhibitors of galectins-1 and -3. Chem. Commun. : 2379-2381.
Glinsky et al. (2009). Synthetic Galectin-3 Inhibitor Increases Metastatic Cancer Cell Sensitivity to Taxol-Induced Apoptosis. In Vitro and In Vivo. Neoplasia 11: 901-909.
Glinksy et al (1996). Inhibition of Human Breast Cancer Metastasis in Nude Mice by Synthetic Glycoamines. Cancer Res. 56:5319-5324.
Grassadonia et al. (2004). 90K (Mac-2 BP) and galectins in tumor progressionnand metastasis. Glycoconjugate J. 19: 551-556.
Hsu et al. (2004). Regulation of cellular homeostasis by galectins. Glycoconjugate J. 19: 507-515.
Huflejt et al. (2004). Galectin-4 in normal tissues and cancer. Glycoconj. J. 20: 247-255.
Ingrassia et al. (2006). A Lactosylated Steroid Contributes in Vivo Therapeutic Benefits in Experimental Models of Mouse Lymphoma and Human Glioblastoma. J. Med. Chem. 49: 1800-1807.
John et al. (2003). Truncated Galectin-3 Inhibits Tumor Growth and Metastasis in Orthotopic Nude Mouse Model of Human Breast. Cancer Clin Cancer Res. 9: 2374-2383.
Lau et al. (2008). N-Glycans in cancer progression. Glycobiology 18: 750-760.
Lau et al. (2007). Complex N-glycan number and degree of branching cooperate to regulate cell proliferation and differentiation. Cell 129: 123-134.
Leffler et al. (2004b). Introduction to Galectins. Glycoconj. J. 19: 433-440.
Leffler Galectins Structure and Function—A Synopsis in Mammalian Carbohydrate Recognition Systems (Crocker, P. ed.) Springer Verlag, Heidelberg, 2001 pp. 57-83.
Leffler et al. (1986). Specificity of binding of three soluble rat lung lectins to substituted and unsubstituted mammalian beta-galactosides. J. Biol. Chem. 261:10119-10126.
Lin et al. (2009). Galectin-3 Targeted Therapy with a Small Molecule Inhibitor Activates Apoptosis and Enhances Both Chemosensitivity and Radiosensitivity in Papillary Thyroid Cancer. Mol Cancer Res 7: 1655-1662.
MacKinnon et al. (2012). Regulation of TGF-β1 driven lung fibrosis by Galectin-3. Am. J. Resp. Crit. Care Med.185:537-546.
MacKinnon et al. (2008). Regulation of alternative macrophage activation by Galectin-3. J. Immun. 180: 2650-2658.
Massa et al. (1993). L-29, an endogenous lectin, binds to glycoconjugate ligands with positive cooperativity. Biochemistry 32: 260-267.
Nangia-Makker et al. (2002). Inhibition of Human Cancer Cell Growth and Metastasis in Nude Mice by Oral Intake of Modified Citrus Pectin. Journal of the National Cancer Institute 94: 1854-1862.
Ocheing et al. (2004). Extracellular functions of galectin-3. Glycoconjugate J 19-527-535.

(56) References Cited

OTHER PUBLICATIONS

Ogawa et al. (2004). The speciation of conger eel galectins by rapid adaptive evolution. Glycoconjugate J. 19: 451-458.
Pace et al. (2004). Insect galectins: Roles in immunity and development. Glycoconjugate J. 19: 607-614.
Pajoohesh-Ganji et al. (2012). Characterization of inflammatory gene expression and galectin-3 function after spinal cord injury in mice. Brain Research 1475:96-105.
Partridge et al. (2004). Regulation of cytokine receptors by Golgi N-glycan processing and endocytosis. Science 306: 120-124.
Patterson et al. (2004). Understanding the biochemical activities of galectin-1 and galectin-3 in the nucleus. Glycoconjugate J. 19: 499-506.
Perone et al. (2009). Suppression of autoimmune diabetes by soluble galectin-1. J Immunol. 182: 2641-2653.
Pienta et al. (1995). Inhibition of spontaneous metastasis in a rat prostate cancer model by oral administration of modified citrus pectin. J. Natl. Cancer Inst. 87: 348-353.
Platt et al. (1992). Modulation of the Lung Colonization of B16-F1 Melanoma Cells by Citrus Pectin. J. Natl. Cancer Inst. 84:439-442.
Pohl et al. (1999). Scope of Multivalent Ligand Function: Lactose-Bearing Neoglycopolymers by Ring-Opening Metathesis Polymerization. Synthesis SI:1515-1519.

* cited by examiner

HYBRID GALACTOSIDE INHIBITOR OF GALECTINS

TECHNICAL FIELD

The present invention relates to novel compounds, the use of said compounds as medicament and for the manufacture of a medicament for treating a disorder relating to the binding of a galectin, such as galectin-3 to a ligand in a mammal, such as a human, in particular for the treatment of pulmonary fibrosis, such as Idiopathic pulmonary fibrosis in mammals. The invention also relates to pharmaceutical compositions comprising said novel compounds.

BACKGROUND ART

Galectins are proteins with a characteristic carbohydrate recognition domain (CRD) (Barondes et al., 1994; Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004)

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Leffler et al., 2004). These were the first discovered galectins and are abundant in many tissues.

There are now over 3500 publications on galectins in PubMed, with most, as mentioned above, about galectins-1 (>900) and -3 (>1600). Strong evidence suggests roles for galectins in e.g. inflammation and cancer, and development recently reviewed in a special issue (Leffler (editor), 2004b).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004). They can also function in all these compartments; for galectin-3, solid evidence published in well respected journals support roles in RNA splicing in the nucleus, inhibition of apoptosis in the cytosol, and a variety of extracellular effects on cell signaling and adhesion (Leffler (editor), 2004b). Galectin-7 and -12 also act in the cytosol by enhancing apoptosis and regulating the cell cycle and differentiation in certain cells (Hsu and Liu in Leffler (editor), 2004b). Most galectins act also extracellularly by cross-linking glycoproteins (e.g. laminin, integrins, and IgE receptors) possibly forming supramolecular ordered arrays (Brewer et al., 2002) and may thereby modulate cell adhesion and induce intracellular signals. Related to this, recent years have seen the emergence of a molecular mechanism of these galectin functions involving a formation of microdomains (lattices) within membranes, (Dam et al., 2008; Garner et al., 2008) which in turn affects intracellular trafficking and cell surface presentation of glycoprotein receptors. (Delacour et al., 2007; Lau et al., 2007; Lau et al. 2008) This has been documented in cell culture, in null mutant mice, (Blois et al., 2007; Gedronneau et al., 2008; Thijssen et al., 2007; Toscano et al., 2007; Saegusa et al., 2009) and animals treated with galectin (Blois et al., 2007; Perone et al., 2009) or galectin inhibitors. (John et al., 2003; Pienta et al., 1995; Glinsky et al., 1996)

Potential Therapeutic Use of Galectin-3 Inhibitors

Galectin-3 has been implicated in diverse phenomena and, hence, inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (nonsteroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation

A pro-inflammatory role of galectin-3 is indicated by its induction in cells at inflammatory sites, a variety of effects on immune cells (e.g. oxidative burst in neutrophils and chemotaxis in monocytes), and decrease of the inflammatory response, mainly in neutrophils and macrophages, in null mutant mice (in Leffler (editor), 2004b). Moreover, knock-out mice of Mac-2BP, a galectin-3 ligand, have increased inflammatory responses (Trahey et al., 1999). Importantly, recent studies have identified galectin-3 as a key rate-limiting factor in macrophage M2 differentiation and myofibroblast activation, which influences the development of fibrosis (Mackinnon et al., 2008; Mackinnon et al., 2012).

Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of the TGF-β receptor (Partridge et al., 2004), which in turn regulates alternative macrophage differentiation into M2 macrophages and myofibroblast activation.

Hence, as galectin-3 is a good candidate for being an endogenous enhancer of TGF-β signaling and alternative macrophage differentiation and myofibroblast activation, galectin-3 inhibitors may be very useful in treating fibrosis and adverse tissue remodeling.

Treatment of Cancer

A large number of immunohistochemical studies show changed expression of certain galectins in cancer (van den Brule et. al. and Bidon et al. in Leffler (editor), 2004b) and for example galectin-3 is now an established histochemical marker of thyroid cancer. The direct evidence for a role of galectin-3 in cancer comes from mouse models, mainly by Raz et al, but also others (in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Lin et al., 2009), as well as in vivo (Glinsky et al., 2009).

Also galectin-1 is frequently over-expressed in low differentiated cancer cells, and galectin-9 or its relatives galectin-4 and galectin-8 may be induced in specific cancer types (Huflejt and Leffler, 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b). Therefore, the over-expression of these galectins in cancers might help the tumor to defend itself against the T-cell response raised by the host.

Null mutant mice for galectins-1 and -3 have been established many years ago (Poirier, 2002). These are healthy and reproduce apparently normally in animal house conditions. However, recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analyzed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Treatment of Angiogenesis

Vascular endothelial growth factors (VEGFs) signaling through VEGF receptor-2 (VEGFR-2) is the primary angiogenic pathway. Studies have been published demonstrating that both galectin-1 (Gal-1) and galectin-3 (Gal-3) are important modulators for VEGF/VEGFR-2 signaling pathway. It has also been published that a galectin inhibitor, TDX, is expected have efficacy against pathological angiogenesis. (Chen 2012)

Known Inhibitors
Natural Ligands

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or LacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

Cluster molecules having up to four lactose moieties showed a strong multivalency effect when binding to galectin-3, but not to galectin-1 and galectin-5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules Thiodigalactoside is known to be a synthetic and hydrolytically stable, yet polar inhibitor, approximately as efficient as N-acetyllactosamine (Leffler and Barondes, 1986). N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 µM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/113569 and US2007185041; WO/2005/113568, U.S. Pat. No. 7,638,623 B2) which lack 0-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamidoand ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

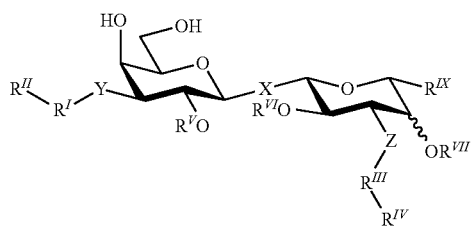

as described in WO/2005/113568,
and

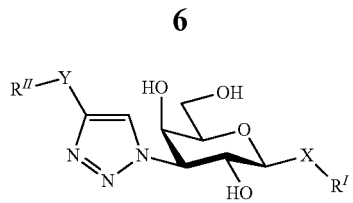

as described in WO/2005/113569, in which $R^I$ can be a D-galactose,
and

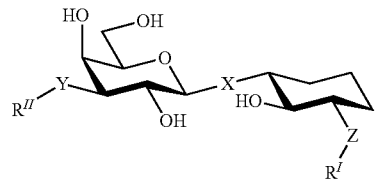

as described in WO/2010/126435.

Thus, due to the less than optimal manufacturing processes towards galactose 3-Nderivatization (Z and Y are preferably nitrogen atoms) involving double inversion reactions at a complex protected D-galactopyranose derivative of the compounds of the prior art, there is still a considerable need within the art of inhibitors against galectins, in particular of galectin-1 and galectin-3.

In recently published US20140099319 and WO2014067986 are disclosed a compound of formula

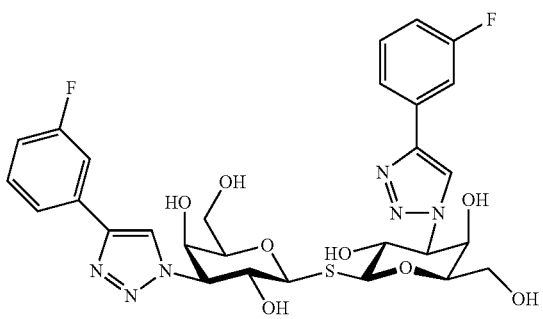

having fluorine in the meta position on both the phenyl rings in relation to the triazole rings. This compound (also referred to as Bis-(3-deoxy-3-(4-(3-fluorophenyl)-1H-1,2,3-triazol-1-yl)β-D-galactopyranosyl) sulfane) has been shown to be a promising drug candidate for lung fibrosis, and in particular is very selective on galectin-3 with high affinity.

SUMMARY OF THE INVENTION

The compounds of the present invention have very high selectivity and affinity for Gal3, in particular have high selectivity over Gal-1, and are considered potent drug candidates.

Several of these compounds have good solubility which is important for making pharmaceutical formulations.

In a broad aspect the present invention relates to a compound of formula (1)

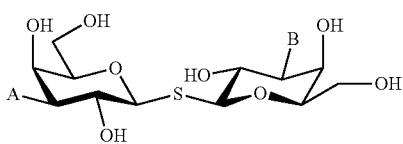

Wherein
A is selected from

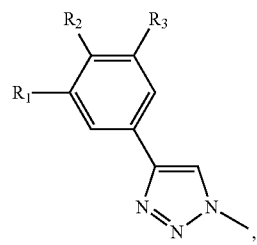

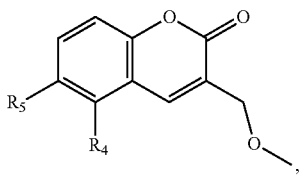

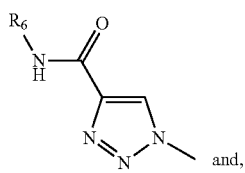

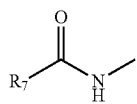

wherein $R_1$-$R_3$ are independently selected from hydrogen (H), fluorine, methyl optionally substituted with a fluorine (F), and $OCH_3$ optionally substituted with a F;
$R_4$ and $R_5$ are independently selected from H, F, Cl and methyl;
$R_6$ is selected from $C_{1-6}$ alkyl, branched $C_{3-6}$ alkyl and C3-C7 cycloalkyl;
$R_7$ is selected from aryl, such as phenyl, naphthyl and anthracenyl, optionally substituted with a F, Cl, methyl optionally substituted with a F, and $OCH_3$ optionally substituted with a F;
B is selected from

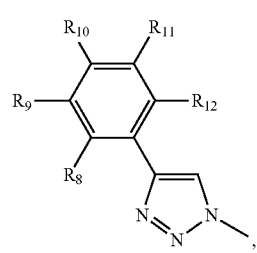

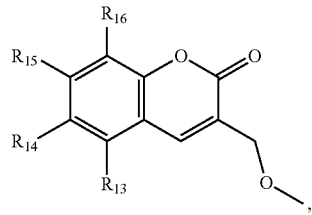

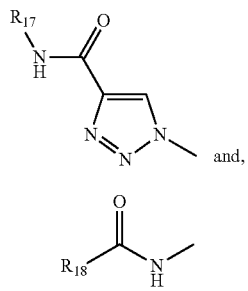

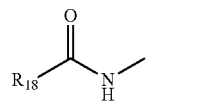

wherein $R_8$-$R_{12}$ are independently selected from H, F, methyl optionally substituted with a fluorine (F), and $OCH_3$ optionally substituted with a F;
$R_{13}$-$R_{16}$ are independently selected from H, F, methyl optionally substituted with a F, and $OCH_3$ optionally substituted with a F;
$R_{17}$ is selected from $C_{1-6}$ alkyl, branched $C_{3-6}$ alkyl and $C_{3-7}$ cycloalkyl;
$R_{18}$ is selected from aryl, such as phenyl, naphthyl and anthracenyl, optionally substituted with a F, Cl, methyl optionally substituted with a F, and $OCH_3$ optionally substituted with a F; or
a pharmaceutically acceptable salt or solvate thereof.

In another aspect the present invention relates to a compound of formula (1) for use as a medicine.

In a further aspect the present invention relates to a pharmaceutical composition comprising the compound of formula (1) and optionally a pharmaceutically acceptable additive, such as carrier or excipient.

In a still further aspect the present invention relates to a compound of formula (1) for use in a method for treating a disorder relating to the binding of a galectin, such as galectin-3 to a ligand in a mammal, such as a human.

In a further aspect the present invention relates to a method for treatment of a disorder relating to the binding of a galectin, such as galectin-3, to a ligand in a mammal, such as a human, wherein a therapeutically effective amount of at least one compound of formula (1) is administered to a mammal in need of said treatment.

In a still further aspect the present invention relates to a process of preparing a compound of formula 1 or a pharmaceutically acceptable salt or solvate thereof comprising the steps a1-a6:

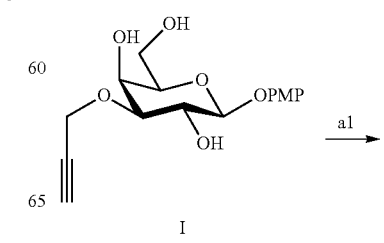

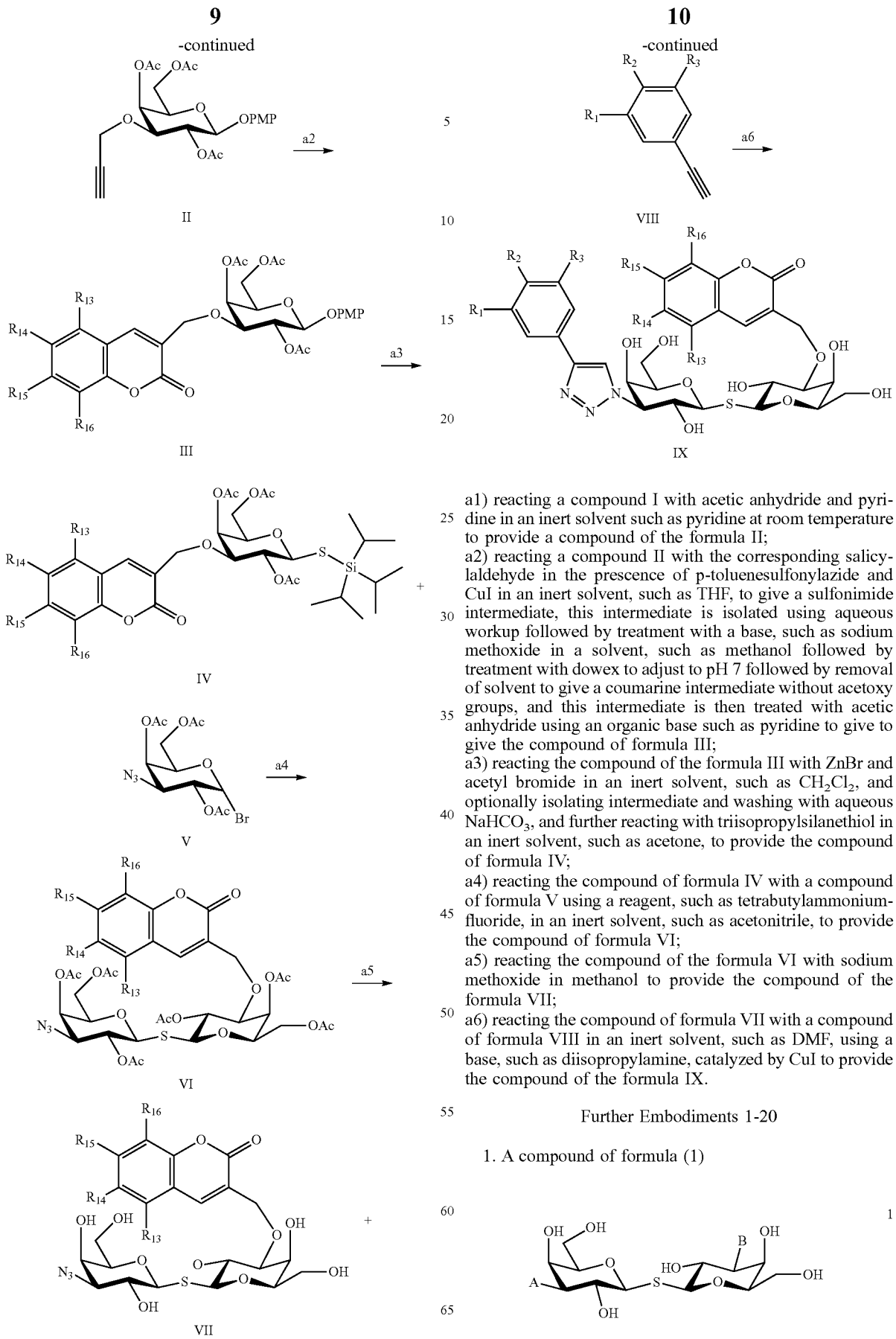

a1) reacting a compound I with acetic anhydride and pyridine in an inert solvent such as pyridine at room temperature to provide a compound of the formula II;

a2) reacting a compound II with the corresponding salicylaldehyde in the prescence of p-toluenesulfonylazide and CuI in an inert solvent, such as THF, to give a sulfonimide intermediate, this intermediate is isolated using aqueous workup followed by treatment with a base, such as sodium methoxide in a solvent, such as methanol followed by treatment with dowex to adjust to pH 7 followed by removal of solvent to give a coumarine intermediate without acetoxy groups, and this intermediate is then treated with acetic anhydride using an organic base such as pyridine to give to give the compound of formula III;

a3) reacting the compound of the formula III with ZnBr and acetyl bromide in an inert solvent, such as $CH_2Cl_2$, and optionally isolating intermediate and washing with aqueous $NaHCO_3$, and further reacting with triisopropylsilanethiol in an inert solvent, such as acetone, to provide the compound of formula IV;

a4) reacting the compound of formula IV with a compound of formula V using a reagent, such as tetrabutylammoniumfluoride, in an inert solvent, such as acetonitrile, to provide the compound of formula VI;

a5) reacting the compound of the formula VI with sodium methoxide in methanol to provide the compound of the formula VII;

a6) reacting the compound of formula VII with a compound of formula VIII in an inert solvent, such as DMF, using a base, such as diisopropylamine, catalyzed by CuI to provide the compound of the formula IX.

Further Embodiments 1-20

1. A compound of formula (1)

Wherein
A is selected from

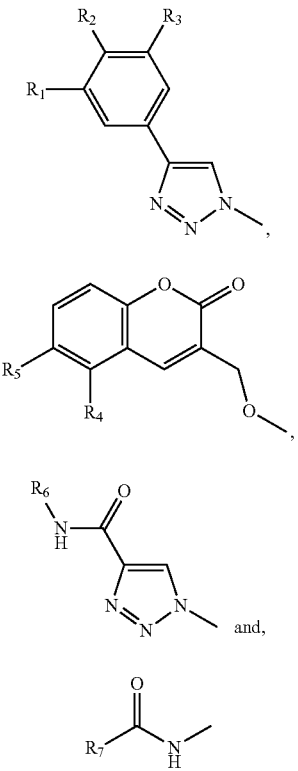

wherein $R_1$-$R_3$ are independently selected from hydrogen (H), fluorine, methyl optionally substituted with a fluorine (F), and $OCH_3$ optionally substituted with a F;

$R_4$ and $R_5$ are independently selected from H, F, Cl and methyl;

$R_6$ is selected from $C_{1-6}$ alkyl, branched $C_{3-6}$ alkyl and $C_{3-7}$ cycloalkyl;

$R_7$ is selected from phenyl optionally substituted with a H, F, Cl, methyl optionally substituted with a F, and $OCH_3$ optionally substituted with a F, 1-Naphtyl optionally substituted with a H, F, Cl, methyl optionally substituted with a F, and $OCH_3$ optionally substituted with a F, or a 2-Naphtyl optionally substituted with a H, F, Cl, methyl optionally substituted with a F, and $OCH_3$ optionally substituted with a F;

B is selected from

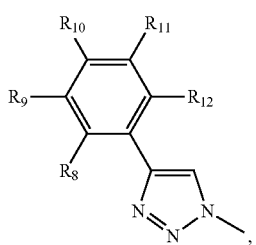

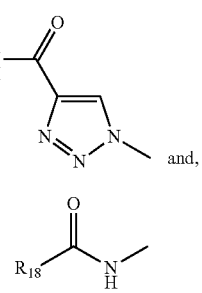

wherein $R_8$-$R_{12}$ are independently selected from H, F, methyl optionally substituted with a fluorine (F), and $OCH_3$ optionally substituted with a F;

$R_{13}$-$R_{16}$ are independently selected from H, F, methyl optionally substituted with a F, and $OCH_3$ optionally substituted with a F;

$R_{17}$ is selected from $C_{1-6}$ alkyl, branched $C_{3-6}$ alkyl and $C_{3-7}$ cycloalkyl;

$R_{18}$ is selected from phenyl optionally substituted with a H, F, Cl, methyl optionally substituted with a F, and $OCH_3$ optionally substituted with a F, 1-Naphtyl optionally substituted with a H, F, Cl, methyl optionally substituted with a F, and $OCH_3$ optionally substituted with a F, or a 2-Naphtyl optionally substituted with a H, F, Cl, methyl optionally substituted with a F, and $OCH_3$ optionally substituted with a F; or a pharmaceutically acceptable salt or solvate thereof; with the proviso that A and B cannot be identical.

2. The compound of embodiment 1 wherein A is selected from formula 2.

3. The compound of embodiment 1 wherein A is selected from formula 2 and B is selected from formula 6.

4. The compound of embodiment 3 wherein $R_1$-$R_3$ are independently selected from H or F, and wherein $R_8$-$R_{12}$ are independently selected from H or F.

5. The compound of embodiment 1 wherein A is selected from formula 2 and B is selected from 7.

6. The compound of embodiment 5 wherein $R_1$-$R_3$ are independently selected from H or F, and wherein $R_{13}$-$R_{14}$ are both F, and $R_{15}$-$R_{16}$ are both H.

7. The compound of embodiment 6 wherein $R_1$ is H, $R_2$ is H, and $R_3$ is F.

8. The compound of embodiment 6 wherein $R_1$-$R_3$ are F.

9. The compound of embodiment 1 wherein A is selected from formula 2 and B is selected from 8.

10. The compound of embodiment 9 wherein $R_1$-$R_3$ are independently selected from H or F, and $R_{17}$ is $C_{1-5}$ alkyl, such as methyl or tert-butyl.

11. The compound of embodiment 9 or 10 wherein $R_1$-$R_3$ are all F, and $R_{17}$ is tert-butyl.

12. The compound of embodiment 1 wherein A is selected from formula 2 and B is selected from 9.

13. The compound of embodiment 12 wherein $R_1$-$R_3$ are independently selected from H or F, and $R_{18}$ is selected from phenyl substituted with four F and one OCH$_3$, such as 2,3,5,6-tetrafluoro-4-methoxy-phenyl; 1-Naphtyl and 2-Naphtyl.

14. The compound of embodiment 12 wherein R$_1$-R$_3$ are all F, and R$_{18}$ is selected from 2,3,5,6-tetrafluoro-4-methoxy-phenyl.

15. The compound of any one of embodiments 1-14 for use as a medicine.

16. A pharmaceutical composition comprising the compound of any one of the previous embodiments and optionally a pharmaceutically acceptable additive, such as carrier or excipient.

17. The compound of any one of the embodiments 1-14 for use in a method for treating a disorder relating to the binding of a galectin, such as galectin-3 to a ligand in a mammal, such as a human.

18. The compound for use according to embodiment 17, wherein said disorder is selected from the group consisting of inflammation; fibrosis, such as pulmonary fibrosis, liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization.

19. A method for treatment of a disorder relating to the binding of a galectin, such as galectin-3, to a ligand in a mammal, such as a human, wherein a therapeutically effective amount of at least one compound according to any one of the embodiments 1-14 is administered to a mammal in need of said treatment.

20. The method of embodiment 19, wherein said disorder is selected from the group consisting of inflammation; fibrosis, such as pulmonary fibrosis, liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization.

Further Embodiments 21-41

21. A compound of formula (I)

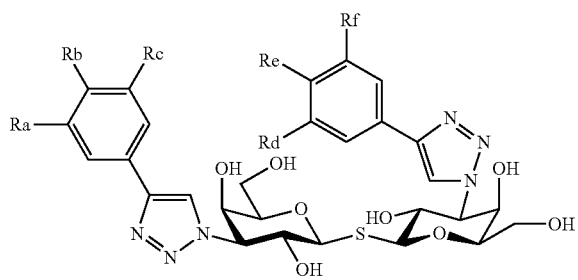

wherein R$_a$-R$_f$ are independently selected from fluorine or hydrogen, and at least three of a$_1$-R$_f$ are F and the remaining are H, or all of R$_a$-R$_f$ are F.

22. The compound of embodiment 21 wherein at least three of R$_a$-R$_f$ are F and the remaining are H.

23. The compound of embodiment 21 wherein at least four of R$_a$-R$_f$ are F and the remaining are H.

24. The compound of embodiment 21 or 22 wherein three of R$_a$-R$_f$ are F and the remaining are H.

25. The compound of embodiment 21 or 23 wherein four of R$_a$-R$_f$ are F and the remaining are H.

26. The compound of embodiment 21 wherein five of R$_a$-R$_f$ are F and the remaining is H.

27. The compound of embodiment 25 wherein R$_a$, R$_b$, R$_d$ and R$_e$ are F and R$_c$ and R$_f$ are H.

28. The compound of embodiment 25 wherein R$_a$, R$_c$, R$_d$ and R$_f$ are F and R$_b$ and R$_e$ are H.

29. The compound of embodiment 25 wherein R$_b$, R$_c$, R$_e$ and R$_f$ are F and R$_a$ and R$_d$ are H.

30. The compound of embodiment 21 wherein all six of R$_a$-R$_f$ are F.

31. The compound of any one of embodiments 21-30 wherein the compound is on free form, such as an anhydrate.

32. The compound of any one of embodiments 21-30 wherein the compound forms a solvate, such as a hydrate.

33. The compound of any one of embodiments 21-32 wherein the compound is on crystalline form, such as a polymorph.

34. The compound of any one of embodiments 21 or 25 wherein the compound of formula I is symmetrical.

35. The compound of any one of embodiments 21-34 for use as a medicine.

36. A pharmaceutical composition comprising the compound of any one of the previous embodiments 1-35 and optionally a pharmaceutically acceptable additive, such as carrier or excipient.

37. The compound of any one of the embodiments 21-34 for use in a method for treating a disorder relating to the binding of a galectin, such as galectin-3 to a ligand in a mammal, such as a human.

38. The compound for use according to embodiment 37, wherein said disorder is selected from the group consisting of inflammation; fibrosis, such as pulmonary fibrosis, liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization.

39. A method for treatment of a disorder relating to the binding of a galectin, such as galectin-3, to a ligand in a mammal, such as a human, wherein a therapeutically effective amount of at least one compound according to any one of the embodiments 21-28 is administered to a mammal in need of said treatment.

40. The method of embodiment 39, wherein said disorder is selected from the group consisting of inflammation; fibrosis, such as pulmonary fibrosis, liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization.

41. A process of preparing a compound of formula I or a pharmaceutically acceptable salt or solvate thereof comprising the steps of a 1,3-dipolar cycloaddition of 1-1'-sulfanediyl-bis[2,4,6-tri-O-acetyl-3-deoxy-3-azido]-β-D-galactopyranoside with fluoro-substituted phenylacetylenes followed by deacetylation to yield the compound of formula I.

DETAILED DESCRIPTION OF THE INVENTION

In a broad aspect the present invention relates to a compound of formula (1)

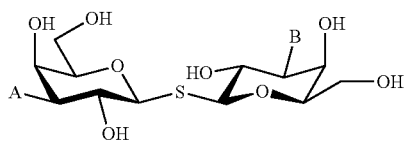

wherein
A is selected from

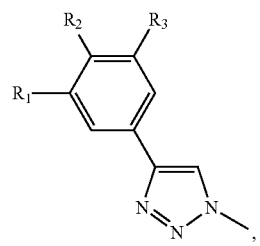

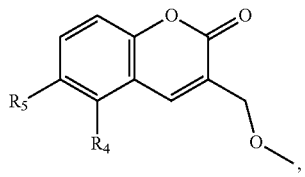

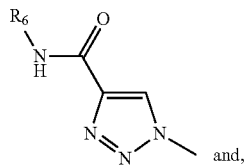

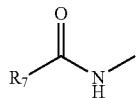

wherein $R_1$-$R_3$ are independently selected from hydrogen (H), fluorine, methyl optionally substituted with a fluorine (F), and $OCH_3$ optionally substituted with a F;

$R_4$ and $R_5$ are independently selected from H, F, Cl and methyl;

$R_6$ is selected from $C_{1-6}$ alkyl, branched $C_{3-6}$ alkyl and $C_{3-7}$ cycloalkyl;

$R_7$ is selected from aryl, such as phenyl, naphthyl and anthracenyl, optionally substituted with a F, Cl, methyl optionally substituted with a F, and $OCH_3$ optionally substituted with a F;

B is selected from

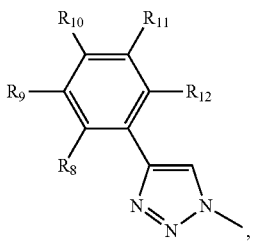

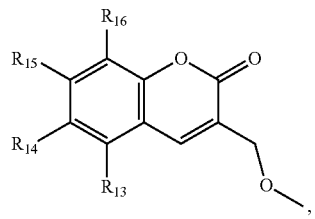

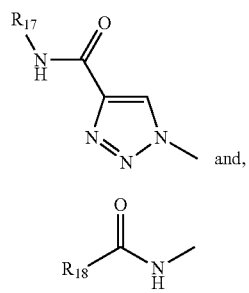

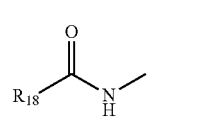

wherein $R_8$-$R_{12}$ are independently selected from H, F, methyl optionally substituted with a fluorine (F), and $OCH_3$ optionally substituted with a F;

$R_{13}$-$R_{16}$ are independently selected from H, F, methyl optionally substituted with a F, and $OCH_3$ optionally substituted with a F;

$R_{17}$ is selected from $C_{1-6}$ alkyl, branched $C_{3-6}$ alkyl and $C_{3-7}$ cycloalkyl;

$R_{18}$ is selected from aryl, such as phenyl, naphthyl and anthracenyl, optionally substituted with a F, Cl, methyl optionally substituted with a F, and $OCH_3$ optionally substituted with a F; or a pharmaceutically acceptable salt or solvate thereof.

In an embodiment A and B cannot be identical. It should be understood that even though A and B cannot be identical this does not exclude compounds of formula 1 wherein A is 2 and B is 6, A is 3 and B is 7, A is 4 and B is 8 and A 5 and B is 9, as long as the formulas 2 and 6, 3 and 7, 4 and 8, and 5 and 9, do not have the same substituent pattern.

The present inventors have realized that the compound of formula (1) creates a stronger binding affinity to galectin-3. The compounds of formula (1) wherein A is selected from formula 2 and B is selected from formula 6-9 provides compounds with good solubility, and in particular compounds of formula 1 wherein A is selected from formula 2 and B is selected from formula 7 have very good affinity to Gal-3 and are selective over Gal-1.

In one embodiment A is selected from formula 2 and B is selected from any one of formulas 6-9.

In an embodiment A is selected from formula 2 and B is selected from formula 6, wherein $R_1$-$R_3$ are independently selected from H and F, and $R_8$-$R_{12}$ are independently selected from H or F.

In a further embodiment A is selected from formula 2 and B is selected from 7, wherein $R_1$-$R_3$ are independently selected from H or F, and $R_{13}$-$R_{14}$ are both F, and $R_{15}$-$R_{16}$ are both H.

In a still further embodiment A is selected from formula 2 and B is selected from 7, wherein $R_1$ is H, $R_2$ is H, and $R_3$ is F, and $R_{13}$-$R_{14}$ are both F, and $R_{15}$-$R_{16}$ are both H.

In a further embodiment A is selected from formula 2 and B is selected from 7, wherein $R_1$-$R_3$ are all F, and $R_{13}$-$R_{14}$ are both F, and $R_{15}$-$R_{16}$ are both H.

In a still further embodiment A is selected from formula 2 and B is selected from 8, wherein $R_1$-$R_3$ are independently selected from H or F, and $R_{17}$ is $C_{1-5}$ alkyl, such as methyl, n-butyl or tert-butyl.

In a further embodiment A is selected from formula 2 and B is selected from 8, wherein $R_1$-$R_3$ are all F, and $R_{17}$ is methyl.

In a still further embodiment A is selected from formula 2 and B is selected from 8, wherein $R_1$-$R_3$ are all F, and $R_{17}$ is tert-butyl.

In another embodiment A is selected from formula 2 and B is selected from 8, wherein $R_1$-$R_3$ are all F, and $R_{17}$ is n-butyl.

In a further embodiment A is selected from formula 2 and B is selected from 9, wherein $R_1$-$R_3$ are independently selected from H or F, and $R_{18}$ is selected from phenyl optionally substituted with a F, Cl, methyl optionally substituted with a F, and $OCH_3$ optionally substituted with a F.

In a further embodiment A is selected from formula 2 and B is selected from 9, wherein $R_1$-$R_3$ are independently selected from H or F, and $R_{18}$ is selected from 1-Naphtyl optionally substituted with a F, Cl, methyl optionally substituted with a F, and $OCH_3$ optionally substituted with a F.

In a further embodiment A is selected from formula 2 and B is selected from 9, wherein $R_1$-$R_3$ are independently selected from H or F, and $R_{18}$ is selected from 2-Naphtyl optionally substituted with a F, Cl, methyl optionally substituted with a F, and $OCH_3$ optionally substituted with a F.

In a further embodiment A is selected from formula 2 and B is selected from 9, wherein $R_1$-$R_3$ are independently selected from H or F, and $R_{18}$ is selected from anthracenyl optionally substituted with a F, Cl, methyl optionally substituted with a F, and $OCH_3$ optionally substituted with a F.

In a further embodiment A is selected from formula 2 and B is selected from 9, wherein $R_1$-$R_3$ are independently selected from H or F, and $R_{18}$ is selected from phenyl substituted with four F and one $OCH_3$, such as 2,3,5,6-tetrafluoro-4-methoxy-phenyl; 1-Naphtyl and 2-Naphtyl.

In a still further embodiment A is selected from formula 2 and B is selected from 9, wherein $R_1$-$R_3$ are independently selected from H or F, and $R_{18}$ is selected from 2,3,5,6-tetrafluoro-4-methoxy-phenyl.

In a further embodiment A is selected from formula 2 and B is selected from 9, wherein $R_1$-$R_3$ are all F, and $R_{18}$ is selected from 2,3,5,6-tetrafluoro-4-methoxy-phenyl.

In a further embodiment A is selected from formula 2 and B is selected from 9, wherein one of $R_1$-$R_3$ is F and the rest is H, and $R_{18}$ is selected from anthracenyl optionally substituted with a F, Cl, methyl optionally substituted with a F, and $OCH_3$ optionally substituted with a F.

In another embodiment A is selected from formula 3 and B is selected from any one of formulas 6-9.

In another embodiment A is selected from formula 4 and B is selected from any one of formulas 6-9.

In another embodiment A is selected from formula 5 and B is selected from any one of formulas 6-9.

In a further aspect the present invention relates to a compound of formula 1 of the present invention for use as a medicine.

In a still further aspect the present invention relates to a pharmaceutical composition comprising a compound of formula 1 of the present invention and optionally a pharmaceutically acceptable additive, such as carrier or excipient.

In a further aspect the present invention relates to a compound of formula 1 of the present invention for use in a method for treating a disorder relating to the binding of a galectin, such as galectin-3 to a ligand in a mammal, such as a human.

In an embodiment the disorder is selected from the group consisting of inflammation; fibrosis, e.g. pulmonary fibrosis, or any solid organ fibrosis e.g. liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization.

In a still further aspect the present invention relates to a method for treatment of a disorder relating to the binding of a galectin, such as galectin-3, to a ligand in a mammal, such as a human, wherein a therapeutically effective amount of at least one compound of formula 1 of the present invention is administered to a mammal in need of said treatment.

In an embodiment the disorder is selected from the group consisting of inflammation; fibrosis, e.g. pulmonary fibrosis, or any solid organ fibrosis e.g. liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization.

In a still further aspect the present invention relates to a process of preparing a compound of formula 1 or a pharmaceutically acceptable salt or solvate thereof comprising the steps b1-b4 below:

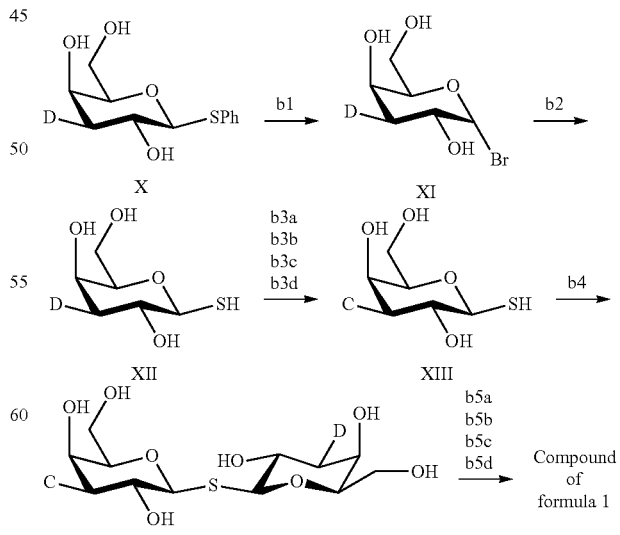

b1) Reacting a compound X wherein D is selected from propargyloxy and azide with bromine in a solvent, such as DCM, to provide a compound of the formula XI;

b2) Reacting the compound of the formula XI with a reagent, such as thiourea in acetonitrile followed by release of the thiol using a base such as triethylamine to provide a compound of formula XII; alternatively the compound of formula XI is reacted with triisopropylsilanethiol in an inert solvent, such as acetone, followed by release of the thiol using tetrabutyl ammoniumfluoride to provide a compound of the formula XII;

b3a) Reacting the compound of formula XII wherein D is selected from azide with a compound of formula VIII or a compound of formula XVII

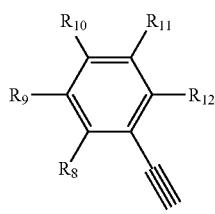

in an inert solvent, such as DMF, using a base, such as diisopropylamine, catalyzed by CuI to provide the compound of the formula XIII wherein C is selected from formula 2 and 6;

b3b) Reacting a compound of formula XII wherein D is selected from propargyloxy with the corresponding salicylaldehyde in the presence of p-toluenesulfonylazide and CuI in an inert solvent, such as THF, to give a sulfonimide intermediate, this intermediate is optionally isolated using aqueous workup, treatment with a base, such as sodium methoxide in methanol followed by treatment with dowex to adjust to pH 7 followed by removal of solvent, and the intermediate is optionally then treated with acetic anhydride using an organic base, such as pyridine to provide a compound of formula XIII wherein D is selected from formula 3 or 7;

b3c) Reacting a compound of formula XII wherein D is selected from azide with methylpropiolate using similar conditions as in step b3a1 to yield a methyl ester, which is reacted with $R_6$—$NH_2$ or $R_{17}$—$NH_2$ to provide a compound of formula XIII wherein C is selected from formula 4 or 8;

b3d) Reacting a compound of the formula XII wherein D is selected from azide with triphenylphosphine in methanol to provide the corresponding amine, which is reacted with $R_7COCl$ or $R_{18}COCl$ using an organic base such as pyridine, DMAP in an inert solvent, such as DCM, to provide a compound of the formula XIII wherein C is selected from formula 5 of 9.

b4) Reacting the compound of formula XIII wherein C is selected from A and B with a compound of formula XI wherein D is selected from propargyloxy and azide using a reagent, such as ammoniumfluoride, in an inert solvent, such as acetonitrile, to provide the compound of formula XV;

b5a) Reacting the compound of formula XV wherein D is selected from azide with a compound of formula (VIII) or (XVII) in an inert solvent, such as DMF, using a base, such as diisopropylamine, catalyzed by CuI to provide the compound of the formula (1) wherein A is selected from formula 2 or B is selected from formula 6;

b5b) Reacting a compound of formula XV wherein D is selected from propargyloxy with the corresponding salicylaldehyde in the prescence of p-toluenesulfonylazide and CuI in an inert solvent, such as THF, to provide a sulfonimide intermediate, which is isolated using aqueous workup, treatment with a base, such as sodium methoxide in methanol followed by treatment with dowex to adjust to pH 7 followed by removal of solvent, which intermediate is then treated with acetic anhydride using an organic base, such as pyridine, to provide a compound of formula (1) wherein A is defined as 3 or B is selected from formula 7.

b5c) Reacting a compound of formula XV wherein D is selected from azide with methylpropiolate using similar conditions as b5a1 to yield a methyl ester, which is reacted with $R_6$—$NH_2$ or $R_{17}$—$NH_2$ to provide a compound of formula 1 wherein A is defined as 4 or B is selected from formula 8.

b5d) Reacting a compound of the formula XV wherein D is selected from azide with triphenylphosphine in methanol to provide the corresponding amine, which amine is then reacted with $R_7COCl$ or $R_{18}COCl$ using an organic base such as pyridine, DMAP in an inert solvent, such as DCM, to provide a compound of the formula 1 wherein A is defined as 5 or B is selected from formula 9.

The skilled person will understand that it may be necessary to adjust or change the order of steps in the process b1-b5, and such change of order is encompassed by the aspects of the process as described above in the reaction schemes and accompanying description of the process steps.

In a further embodiment the present invention relates to a compound, which is selected from 3'-Deoxy-3-O-[(5,6-difluoro-2-oxo-3-chromenyl)methyl]-3'-[4-(3-fluorophenyl)-1H-1,2,3-triazol-1-yl]-1,1'-sulfanediyl-di-β-D-galactopyranoside, 3'-Deoxy-3-O-[(5,6-difluoro-2-oxo-3-chromenyl)methyl]-3'-[4-(3,4,5-trifluorophenyl)-1H-1,2,3-triazol-1-yl]-1,1'-sulfanediyl-di-β-D-galactopyranoside, 3'-{4-[(Butylamino)carbonyl]-1H-1,2,3-triazol-1-yl}-3'deoxy-3-O-[(5,6-difluoro-2-oxo-3-chromenyl)methyl]-1,1'-sulfanediyl-di-β-D-galactopyranoside, 3-{4-[(Butylamino)carbonyl]-1H-1,2,3-triazol-1-yl}-3,3'-dideoxy-3'-[4-(3,4,5-trifluorophenyl)-1H-1,2,3-triazol-1-yl]-1,1'-sulfanediyl-di-β-D-galactopyranoside, 3,3'-Dideoxy-3'-[4-(3-fluorophenyl)-1H-1,2,3-triazol-1-yl]-3-(4-methoxy-2,3,5,6-tetrafluoro-benzamido)-1,1'-sulfanediyl-di-β-D-galactopyranoside, 3-(9-anthracene carboxamide)-3,3'-Dideoxy-3-[4-(3-fluorophenyl)-1H-1,2,3-triazol-1-yl]-1,1'-sulfanediyl-di-β-D-galactopyranoside, 3-(2-anthracene carboxamide)-3,3'-Dideoxy-3-[4-(3-fluorophenyl)-1H-1,2,3-triazol-1-yl]-1,1'-sulfanediyl-di-β-D-galactopyranoside, 3,3'-Dideoxy-3-[4-(3,4,5-trifluorophenyl)-1H-1,2,3-triazol-1-yl]-3'-[4-phenyl-1H-1,2,3-triazol-1-yl]-1,1'-sulfanediyl-di-β-D-galactopyranoside, 3,3'-dideoxy-3,3'-di-[4-(3,4-difluorophenyl)-1H-1,2,3-triazol-1-yl]-1,1'-sulfanediyl-di-β-D-galactopyranoside, 3,3'-bisdeoxy-3,3'-bis-[4-(3,4,5-trifluorophenyl)-1H-1,2,3-triazol-1-yl]-1,1'-sulfanediyl-di-β-D-galactopyranoside, and 3,3'-bisdeoxy-3,3'-bis-[4-(3,5-difluorophenyl)-1H-1,2,3-triazol-1-yl]-1,1'-sulfanediyl-di-β-D-galactopyranoside.

In a more specific embodiment of the compound of formula (1) the present invention relates to a compound of formula (I)

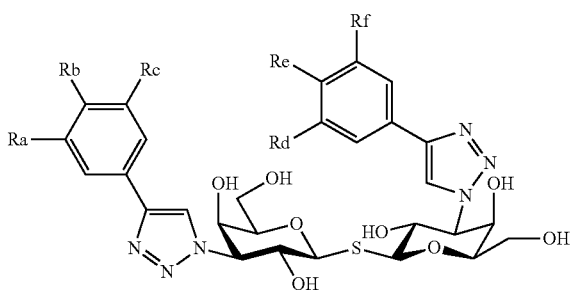

wherein $R_a$-$R_f$ are independently selected from fluorine or hydrogen, and at least three of $R_a$-$R_f$ are F and the remaining are H, or all of $R_a$-$R_f$ are F.

The present inventors have realized that having several F substituents in one or both phenyl groups of the compound of formula (I) creates a stronger binding affinity to galectin-3.

In an embodiment at least three of $R_a$-$R_f$ are F and the remaining are H.

In another embodiment at least four of $R_a$-$R_f$ are F and the remaining are H.

In a further embodiment three of $R_a$-$R_f$ are F and the remaining are H. In one embodiment $R_a$, $R_b$, $R_c$ are F and $R_d$, $R_e$ and $R_f$ are H. In a further embodiment $R_a$, $R_b$, $R_d$ are F and $R_c$, $R_e$ and $R_f$ are H. In a still further embodiment $R_a$, $R_b$, $R_e$ are F and $R_c$, $R_d$ and $R_f$ are H. In a further embodiment $R_a$, $R_b$, $R_f$ are F and $R_c$, $R_d$ and $R_e$ are H. In a still further embodiment $R_a$, $R_c$, $R_d$ are F and $R_b$, $R_e$ and $R_f$ are H. In a further embodiment $R_a$, $R_c$, $R_e$ are F and $R_b$, $R_d$ and $R_f$ are H. In a still further embodiment $R_a$, $R_c$, $R_f$ are F and $R_b$, $R_d$ and $R_e$ are H. In a further embodiment $R_b$, $R_c$, $R_d$ are F and $R_a$, $R_e$ and $R_f$ are H. In a further embodiment $R_b$, $R_c$, $R_e$ are F and $R_a$, $R_d$ and $R_f$ are H. In a still further embodiment $R_b$, $R_c$, $R_f$ are F and $R_a$, $R_d$ and $R_e$ are H. In a further embodiment $R_a$, $R_b$, $R_d$ are H and $R_c$, $R_e$ and $R_f$ are F. In a still further embodiment $R_a$, $R_b$, $R_e$ are H and $R_c$, $R_d$ and $R_f$ are F. In a further embodiment $R_a$, $R_b$, $R_f$ are H and $R_c$, $R_d$ and $R_e$ are F. In a still further embodiment $R_a$, $R_c$, $R_d$ are H and $R_b$, $R_e$ and $R_f$ are F. In a further embodiment $R_a$, $R_c$, $R_e$ are H and $R_b$, $R_d$ and $R_f$ are F. In a still further embodiment $R_a$, $R_c$, $R_f$ are H and $R_b$, $R_d$ and $R_e$ are F. In a further embodiment $R_b$, $R_c$, $R_d$ are H and $R_a$, $R_e$ and $R_f$ are F. In a further embodiment $R_b$, $R_c$, $R_e$ are H and $R_a$, $R_d$ and $R_f$ are F. In a still further embodiment $R_b$, $R_c$, $R_f$ are H and $R_a$, $R_d$ and $R_e$ are F. In a further embodiment $R_a$, $R_b$, $R_c$ are H and $R_d$, $R_e$ and $R_f$ are F.

In a further embodiment four of $R_a$-$R_f$ are F and the remaining are H. In one embodiment $R_a$, $R_b$, $R_c$, $R_d$ are F and $R_e$ and $R_f$ are H. In a further embodiment $R_a$, $R_b$, $R_c$, $R_e$, are F and $R_d$ and $R_f$ are H. In a still further embodiment $R_a$, $R_b$, $R_c$, $R_f$ are F and $R_d$ and $R_e$ are H. In a further embodiment $R_a$, $R_d$, $R_e$, $R_f$ are F and $R_b$ and $R_c$ are H. In a still further embodiment $R_b$, $R_d$, $R_e$, $R_f$ are F and $R_a$ and $R_c$ are H. In a further embodiment $R_c$, $R_d$, $R_e$, $R_f$ are F and $R_a$ and $R_b$ are H. In a still further embodiment $R_a$, $R_b$, $R_d$, $R_e$ are F and $R_c$ and $R_f$ are H. In a further embodiment $R_a$, $R_b$, $R_d$, $R_f$ are F and $R_c$ and $R_e$ are H. In a still further embodiment $R_a$, $R_b$, $R_e$, $R_f$ are F and $R_c$ and $R_d$ are H. In a further embodiment $R_a$, $R_c$, $R_d$, $R_e$ are F and $R_b$ and $R_f$ are H. In a still further embodiment $R_a$, $R_c$, $R_d$, $R_f$ are F and $R_b$ and $R_e$ are H. In a further embodiment $R_a$, $R_c$, $R_e$, $R_f$ are F and $R_b$ and $R_d$ are H. In a still further embodiment $R_b$, $R_c$, $R_d$, $R_f$ are F and $R_a$ and $R_e$ are H. In a further embodiment $R_b$, $R_c$, $R_e$, $R_f$ are F and $R_a$ and $R_d$ are H. In a still further embodiment $R_b$, $R_c$, $R_d$, $R_e$ are F and $R_a$ and $R_f$ are H. In a further embodiment $R_b$, $R_c$, $R_e$, $R_f$ are F and $R_a$ and $R_d$ are H.

In a further embodiment five of $R_a$-$R_f$ are F and the remaining is H. In one embodiment $R_a$, $R_b$, $R_c$, $R_d$, $R_e$ are F and $R_f$ is H. In a further embodiment $R_a$, $R_b$, $R_c$, $R_d$, $R_f$ are F and $R_e$ is H. In a still further embodiment $R_a$, $R_b$, $R_c$, $R_e$, $R_f$ are F and $R_d$ is H. In a further embodiment $R_a$, $R_b$, $R_d$, $R_e$, $R_f$ are F and $R_c$ is H. In a still further embodiment $R_a$, $R_c$, $R_d$, $R_e$, $R_f$ are F and $R_b$ is H. In a further embodiment $R_b$, $R_c$, $R_d$, $R_e$, $R_f$ are F and $R_a$ is H.

In a further embodiment all six of $R_a$-$R_f$ are F.

In a still further embodiment the compound of formula I is symmetrical, which means that the two D-galactose groups substituted with a phenyl substituted triazol attached to the sulphur atom (S) are identical.

In a still further embodiment the compound of formula I is on free form. In one embodiment the free form is an anhydrate. In another embodiment the free form is a solvate, such as a hydrate.

In a further embodiment the compound of formula I is on crystalline form. The skilled person may carry out tests in order to find polymorphs, and such polymorphs are intended to be encompassed by the term "crystalline form" as used herein.

In a further aspect the present invention relates to a compound of formula (I)

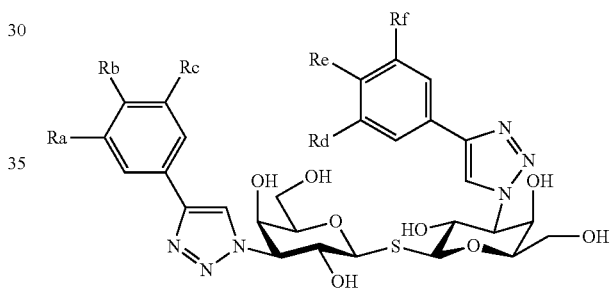

wherein $R_a$-$R_f$ are independently selected from fluorine or hydrogen, and at least three of $R_a$-$R_f$ are F and the remaining are H, or all of $R_a$-$R_f$ are F, for use as a medicine.

In a still further aspect the present invention relates to a compound of formula (I)

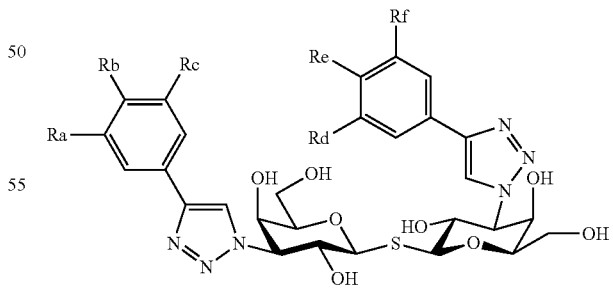

wherein $R_a$-$R_f$ are independently selected from fluorine or hydrogen, and at least three of $R_a$-$R_f$ are F and the remaining are H, or all of $R_a$-$R_f$ are F, for use in a method for treating a disorder relating to the binding of a galectin, such as galectin-3 to a ligand in a mammal, such as a human. In one embodiment the disorder is selected from the group consisting of inflammation; fibrosis, such as pulmonary fibrosis, liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization. In particular the disorder is fibrosis, such as pulmonary fibrosis, liver fibrosis, kidney fibrosis, ophtalmological fibrosis and fibrosis of the heart.

In a further aspect the present invention relates a method for treatment of a disorder relating to the binding of a galectin, such as galectin-3, to a ligand in a mammal, such as a human, wherein a therapeutically effective amount of at least one compound of formula (I)

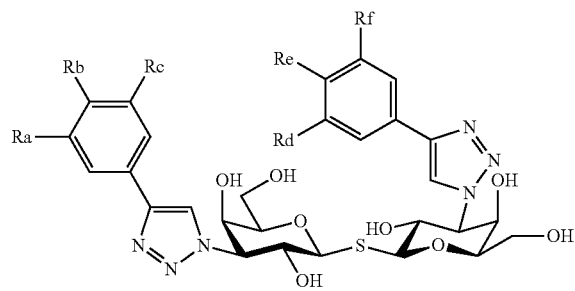

wherein $R_a$-$R_f$ are independently selected from fluorine or hydrogen, and at least three of $R_a$-$R_f$ are F and the remaining are H, or all of $R_a$-$R_f$ are F, is administered to a mammal in need of said treatment. In one embodiment the disorder is selected from the group consisting of inflammation; fibrosis, such as pulmonary fibrosis, liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization.

A process of preparing a compound of formula I or a pharmaceutically acceptable salt or solvate thereof comprising the steps of a 1,3-dipolar cycloaddition of 1-1'-sulfanediyl-bis[2,4,6-tri-O-acetyl-3-deoxy-3-azido]-β-D-galactopyranoside (A1) with fluoro-substituted phenylacetylenes followed by deacetylation to yield the compound of formula I. In one embodiment deacetylation is carried out with a mixture of NaOMe and MeOH.

Furthermore the skilled person will understand that the processes described above and herein-after the functional groups of intermediate compounds may need to be protected by protecting group.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g, t-butyldimethylsilyl, t-butyldipheylsilyl or trimethylsilyl), AcO, TBS, TMS, PMB, and tetrahydropyranyl. Suitable protecting groups for carboxylic acid include (C1-C6)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)NH$_2$, TIPS.

The protection and deprotection of functional groups may take place before or after any reaction in the above mentioned processes.

Furthermore the skilled person will appreciate that, in order to obtain compounds of the invention in an alternative, and on some occasions, more convenient, manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound of formula (1) is on free form. In one embodiment the free form is an anhydrate. In another embodiment the free form is a solvate, such as a hydrate.

In a further embodiment the compound of formula (1) is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "$C_{1-6}$ alkyl" as used herein means an alkyl group containing 1-6 carbon atoms, such as methyl, ethyl, propyl, butyl, pentyl or hexyl.

The term "branched $C_{3-6}$ alkyl" as used herein means a branched alkyl group containing 3-6 carbon atoms, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "aryl" as used herein means an aromatic carbon group containing 6-16 carbon atoms, and no heteroatoms in the ringsystem, including but not limited to phenyl, naphthyl, anthracenyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context. For instance, when it is stated "optionally substituted with a" it means "optionally substituted with one or more".

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Section 1

Evaluation of Kd Values

The affinity of compounds S8a-c, S11, S16, S20a-b and S21 for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47, (Sörme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al., 2010). The assay was adapted to be able to measure the high affinity of the present compound for galectin-3 by using a probe (SY) constructed to have high affinity for galectin-3 based on the structure of 3,3'-Dideoxy-3,3'-di-[4-(3-fluorophenyl)-1H-1,2,3-triazol-1-yl]-1,1'-sulfanediyl-di-β-D-galactopyranoside, which made it possible to use a low concentration of galectin-3 (50 nM). 100 nM albumin was included as a carrier to prevent protein loss at such low concentration of galectin.

Compounds of the type S8a-c were found to be less active towards galectin-1 as compared to 3,3'-Dideoxy-3,3'-di-[4-(3-fluorophenyl)-1H-1,2,3-triazol-1-yl]-1,1'-sulfanediyl-di-β-D-galactopyranoside (structure below) and as a consequence therefore more selective towards Galectin-3.

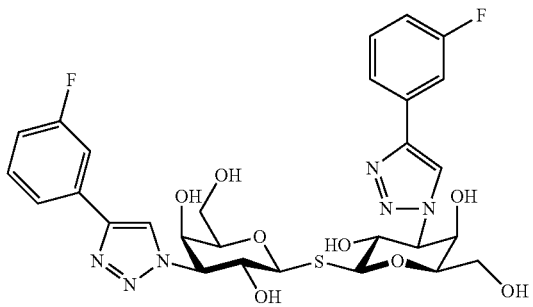

SX

Kd values for compounds 8a-c, S11, S16, S20a-b and S21 and reference compound 3,3'-Dideoxy-3,3'-di-[4-(3-fluorophenyl)-1H-1,2,3-triazol-1-yl]-1,1'-sulfanediyl-di-β-D-galactopyranoside (SX)

| Example | Galectin-1 Kd (µM) | Galectin-3 Kd (µM) |
| --- | --- | --- |
| S8a | 0.32 | 0.028 |
| S8b | 0.48 | 0.002 |
| S8c | 1.2 | 0.072 |
| S11 | 0.077 | 0.001 |
| S16 | 0.09 | 0.007 |
| S20a | 0.38 | 0.064 |
| S20b | 0.49 | 0.14 |
| S21 | 0.066 | 0.003 |
| SX | 0.060 | 0.001 |

Synthesis of Examples

Materials and Methods

NMR spectra were recorded on a Bruker Avance II 400 MHz spectrometer at ambient temperature. ¹H-NMR spectra were assigned using 2D-methods (COSY). Chemical shifts are given in ppm downfield from the signal for Me₄Si, with

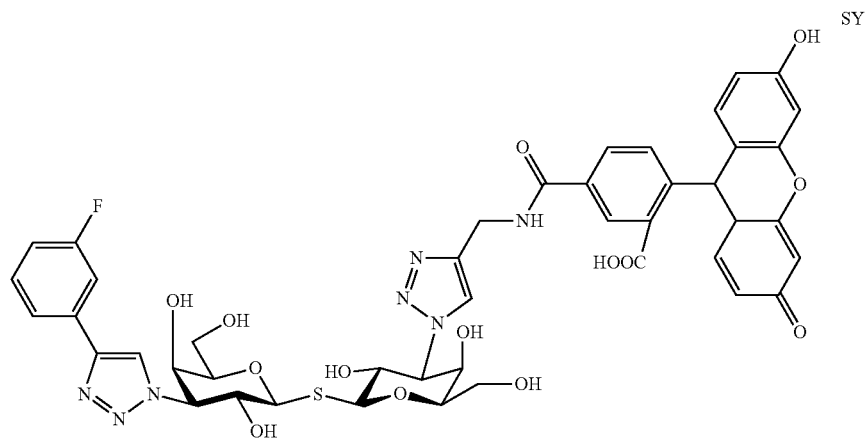

SY reference to residual CHCl₃ or CD₂HOD. HRMS was determined by direct infusion on a Waters XEVO-G2 QTOF mass spectrometer using electrospray ionization (ESI). Reactions were monitored by TLC using aluminum-backed silica gel plates (Merck 60F$_{254}$) and visualized using UV light and by charring with ethanolic H$_2$SO$_4$ (7%). Column chromatography was performed using silica gel (40-60 μm, 60 Å) columns. Solvents were dried by storing over activated M.S. Reagents were supplied by Sigma-Aldrich and used as it is.

Examples 1-3

Example 1

S8a) 3'-Deoxy-3-O-[(5,6-difluoro-2-oxo-3-chromenyl)methyl]-3'-[4-(3-fluorophenyl)-1H-1,2,3-triazol-1-yl]-1,1'-sulfanediyl-di-β-D-galactopyranoside To a solution of S7 (90 mg, 0.16 mmol) and CuI (3 mg, 0.016 mmol) in DMF (8 mL) was 1-ethynyl-3-fluorobenzene (0.036 mL, 0.31 mmol) added followed by diisopropylethylamine (0.027 mL, 0.16 mmol). The resulting suspension was stirred at rt for 6 h followed by 90 min at 50° C. to get full conversion of starting material. The solution

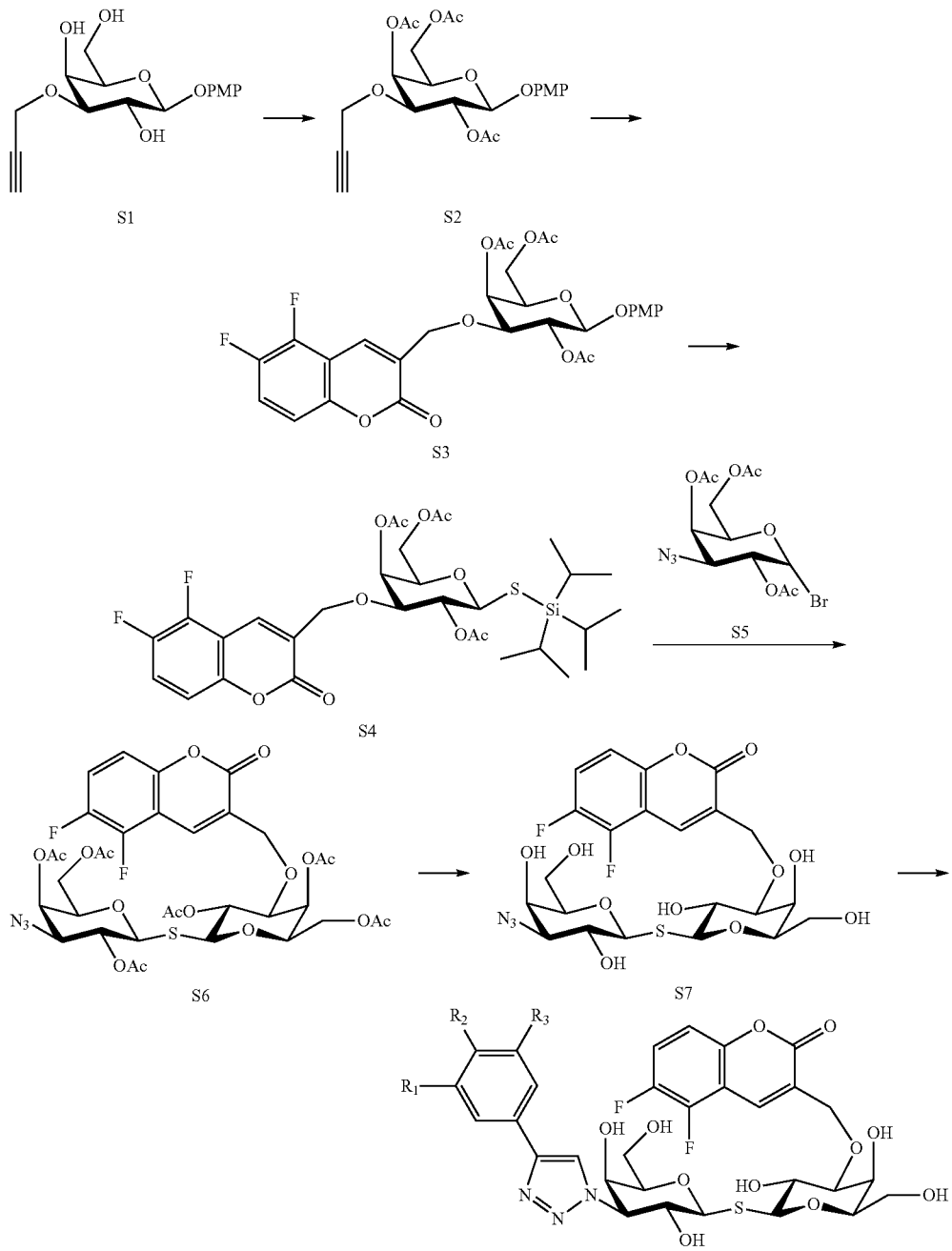

was evaporated on silica gel and purified with flash chromatography (CH$_2$Cl$_2$:MeOH 19:1→14:1) to give S8a (48 mg, 44%). $^1$H-NMR (MeOD, 400 MHz) δ 8.52 (s, 1H), 8.39 (s, 1H), 7.66 (d, J=7.7 Hz, 1H), 7.60 (d, J=10.0 Hz, 1H), 7.53-7.42 (m, 2H), 7.20 (d, J=9.4 Hz, 1H), 7.07 (td, J=8.4, 2.3 Hz, 1H), 4.95 (d, J=9.6 Hz, 1H), 4.88 (dd, J=10.7, 3.0 Hz, 1H), 4.77 (d, J=9.9 Hz, 1H), 4.73 (dd, J=15.4, 1.5 Hz, 1H), 4.63 (dd, J=15.4, 1.5 Hz, 1H), 4.43 (t, J=10.4 Hz, 1H), 4.22 (d, J=2.7 Hz, 1H), 4.13 (d, J=2.7 Hz, 1H), 3.97 (t, J=9.6 Hz, 1H), 3.87-3.79 (m, 3H), 3.75-3.63 (m, 3H), 3.53 (dd, J=9.2, 3.1 Hz, 1H).

HRMS calcd for [C$_{30}$H$_{30}$F$_3$N$_3$O$_{11}$NaS]$^+$, 720.1451; found: 720.1443.

Example 2

S8b) 3'-Deoxy-3-O-[(5,6-difluoro-2-oxo-3-chromenyl)methyl]-3'-[4-(3,4,5-trifluorophenyl)-1H-1,2,3-triazol-1-yl]-1,1'-sulfanediyl-di-β-D-galactopyranoside To a solution of S7 (26 mg, 0.045 mmol) and CuI (1 mg, 0.0045 mmol) in DMF (4 mL) was added 3,4,5-trifluorophenylacetylene (0.009 mL, 0.090 mmol) followed by diisopropylethylamine (0.008 mL, 0.045 mmol). The resulting suspension was stirred at 50° C. for 3 h. The solution was evaporated on silica gel and purified with flash chromatography (CH$_2$Cl$_2$:MeOH 19:1→14:1) to give S8b (15 mg, 45%).

$^1$H-NMR (MeOD, 400 MHz) δ 8.55 (s, 1H), 8.38 (s, 1H), 7.63 (dd, J=8.9, 6.6 Hz, 2H), 7.50 (q, J=9.1 Hz, 1H), 7.20 (d, J=9.2 Hz, 1H), 4.94 (d, J=9.6 Hz, 1H), 4.88 (dd, J=9.8, 3.0 Hz, 1H), 4.77 (d, J=9.9 Hz, 1H), 4.73 (dd, J=15.4, 1.5 Hz, 1H), 4.63 (dd, J=15.4, 1.5 Hz, 1H), 4.40 (t, J=9.6 Hz, 1H), 4.22 (d, J=2.7 Hz, 1H), 4.12 (d, J=2.8 Hz, 1H), 3.96 (t, J=9.6 Hz, 1H), 3.86-3.79 (m, 3H), 3.75-3.67 (m, 2H), 3.64 (m, 1H), 3.53 (dd, J=9.2, 3.1 Hz, 1H).

HRMS calcd for [C$_{30}$H$_{29}$F$_5$N$_3$O$_{11}$S]$^+$, 734.1443; found: 734.1453.

Example 3

S8c) 3'-{4-[(Butylamino)carbonyl]-1H-1,2,3-triazol-1-yl}-3'deoxy-3-O-[(5,6-difluoro-2-oxo-3-chromenyl)methyl]-1,1'-sulfanediyl-di-β-D-galactopyranoside

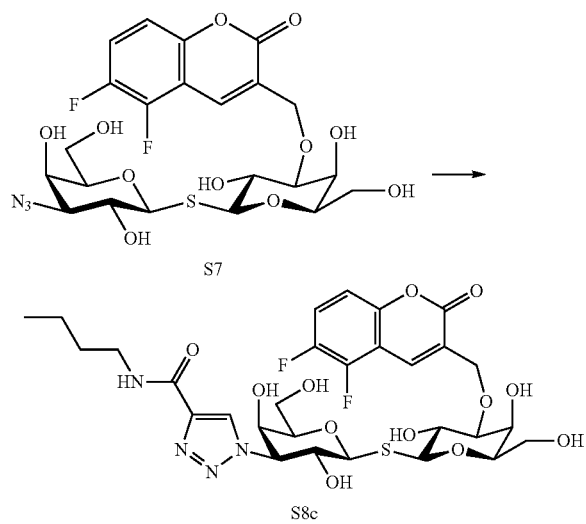

Compound S7 (60 mg, 0.104 mmol) was dissolved in acetic anhydride (3 mL) and pyridine (3 mL), stirred at rt o.n. The volatiles were evaporated and the obtained residue followed by addition of CuI (4.9 mg, 0.026 mmol) and acetonitrile (4 mL). Methyl propiolate (0.014 mL, 0.156 mmol) was added followed by diisopropylethylamine (0.018 mL, 0.104 mmol) and the mixture was stirred at 50° C. for 4 h. The solvent was evaporated and obtained residue was stirred with a solution of butylamine 20% in MeOH for 6 days at rt. The solution was evaporated and the residue was purified with flash chromatography (CH$_2$Cl$_2$:MeOH 19:1→9:1) to give S8c (0.3 mg, 0.4%).

HRMS calcd for [C$_{29}$H$_{37}$F$_2$N$_4$O$_{12}$S]$^+$, 703.2090; found: 703.2097.

Preparation of Starting Materials Examples 1-3

S2) 4-Methoxyphenyl 2,4,6-tri-O-acetyl-3-O-propargyl-β-D-galactopyranoside

Compound S1 (1.45 g, 4.48 mmol) (L. Zhang, G. Wei, Y. Du, *Carbohydr. Res.,* 2009, 344, 2083-2087) was dissolved in acetic anhydride (10 mL) and pyridine (10 mL) and stirred at rt (room temperature) o.n. (over night) The solvent was evaporated to give S2 (2.01 g, 99%) as a white solid.

$^1$H-NMR (CDCl$_3$, 400 MHz) δ 6.96 (d, J=9.1 Hz, 2H), 6.81 (d, J=9.1 Hz, 2H), 5.44 (d, J=2.5 Hz, 1H), 5.31 (dd, J=10.0, 8.0 Hz, 1H), 4.91 (d, J=8.0 Hz, 1H), 4.20 (m, 2H), 3.95 (t, J=6.5 Hz, 1H), 3.90 (dd, J=10.0, 3.5 Hz, 1H), 3.77 (s, 3H), 2.17 (s, 3H), 2.12 (s, 3H), 2.08 (s, 3H).

HRMS calcd for [C$_{22}$H$_{26}$O$_{10}$Na]$^+$, 473.1424; found: 473.1426.

S3) 4-Methoxyphenyl 2,4,6-tri-O-acetyl-3-O-[(5,6-difluoro-2-oxo-3-cromenyl)methyl]-β-D-galactopyranoside To a mixture of S2 (1.23 g, 2.72 mmol), 5,6-difluorosalicylaldehyde (860 mg, 5.44 mmol) and CuI (518 mg, 2.72 mmol) in THF (100 mL) was p-toluenesulfonyl azide (1.34 g, 6.80 mmol) dissolved in THF (5 mL) added. The resulting mixture was stirred for 30 min before triethylamine (1.51 mL, 10.88 mmol) was added and the resulting solution was stirred for 1 h at rt. After evaporation of the solvent was the residue diluted with CH$_2$Cl$_2$ and washed with sat. aq. NH$_4$Cl and brine. The organic phase was dried and evaporated, after which the obtained residue was dissolved in MeOH (75 mL) and NaOMe (1 M, 25 mL). The resulting solution was stirred o.n. followed by addition of Dowex to adjust pH to 7 and the solution was concentrated. The obtained residue was dissolved in acetic anhydride (10 mL) and pyridine (10 mL) and stirred at rt for 5 h. Evaporation of the solvents and purification by column chromatography (heptane:EtOAc 3:1→1:1) gave S3 (1.35 g, 82%).

$^1$H-NMR (CDCl$_3$, 400 MHz) δ 7.91 (s, 1H), 7.33 (q, J=9.4 Hz, 1H), 7.09 (d, J=9.3 Hz, 1H), 6.96 (d, J=9.1 Hz, 2H), 6.82 (d, J=9.1 Hz, 2H), 5.57 (d, J=2.5 Hz, 1H), 5.45 (dd, J=10.0, 7.9 Hz, 1H), 4.90 (d, J=8.0 Hz, 1H), 4.67 (dd, J=14.5, 1.5 Hz, 1H), 4.48 (dd, J=14.5, 1.5 Hz, 1H), 4.28-4.18 (m, 2H), 3.97 (t, J=6.4 Hz, 1H), 3.78 (s, 3H), 3.76 (dd, J=10.1, 3.4 Hz, 1H), 2.20 (s, 3H), 2.12 (s, 3H), 2.08 (s, 3H).

S4) Triisopropylsilyl 2,4,6-tri-O-acetyl-3-O-[(5,6-difluoro-2-oxo-3-cromenyl)methyl]-1-thio-β-D-galactopyranoside Zinc bromide (25 mg, 0.11 mmol) and S3 (1.35 g, 2.23 mmol) were dissolved in CH$_2$Cl$_2$ (50 mL) and acetyl bromide (0.49 mL, 6.68 mmol) was added, the solution was stirred for 14 h at rt. The solution was diluted with CH$_2$Cl$_2$ and washed three times with sat. aq. NaHCO$_3$ and three times with brine. The organic phase was dried and evaporated. The obtained residue and K$_2$CO$_3$ (769 mg, 5.57 mmol) were dissolved in acetone (40 mL) and triisopropylsilanethiol (0.60 mL, 2.78 mmol) was added. The solution was stirred 18 h at rt followed by evaporation of the solvent, CH$_2$Cl$_2$ was added and it was washed with water. The organic phase was dried, evaporated and the residue purified with flash chromatography (heptane:EtOAc 4:1→1:1) to obtain S4 (566 mg, 38%).

$^1$H-NMR (CDCl$_3$, 400 MHz) δ 7.88 (s, 1H), 7.32 (q, J=9.4 Hz, 1H), 7.08 (d, J=7.3 Hz, 1H), 5.55 (d, J=2.5 Hz, 1H), 5.25 (t, J=9.7 Hz, 1H), 4.63 (m, 2H, H–1), 4.43 (dd, J=14.5, 1.5 Hz, 1H), 4.14 (m, 2H), 3.82 (t, J=6.3 Hz, 1H), 3.65 (dd, J=9.7, 3.4 Hz, 1H), 2.17 (s, 3H), 2.10 (s, 3H), 2.06 (s, 3H), 1.27 (m, 3H), 1.13 (d, J=6.4 Hz, 18H).

S6) 2,4,6-Tri-O-acetyl-3-O-[(5,6-Difluoro-2-oxo-3-chromenyl)methyl]-2',4',6'-tri-O-acetyl-3'-azido-3'-deoxy-1,1'-sulfanediyl-di-β-D-galactopyranoside Compounds S4 (537 mg, 0.80 mmol) and S5 (370 mg, 0.94 mmol) (T. L. Lowary, O. Hindsgaul, Carbohydr. Res., 1994, 251, 33-67) were dissolved in acetonitrile (30 mL) and nitrogen gas was bubbled through the solution for 10 min after which tetrabutylammonium fluoride (0.84 mL, 1 M in THF, 0.84 mmol) was added. After 2.5 h was the solvent removed, the residue was dissolved in CH$_2$Cl$_2$ and washed with water. The organic phase was dried, evaporated and purified with flash chromatography (heptane:EtOAc 3:1→1:2) to give S6 (652 mg, 98%).

$^1$H-NMR (CDCl$_3$, 400 MHz) δ 7.86 (s, 1H), 7.33 (q, J=9.3 Hz, 1H), 7.09 (m, 1H), 5.58 (d, J=3.1 Hz, 1H), 5.48 (d, J=2.9 Hz, 1H), 5.21 (t, J=10.1 Hz, 1H), 5.19 (t, J=10.2 Hz, 1H), 4.81 (d, J=10.0 Hz, 1H), 4.79 (d, J=10.0 Hz, 1H), 4.64 (dd, J=14.5, 1.5 Hz, 1H), 4.46 (dd, J=14.3, 1.3 Hz, 1H), 4.23-4.11 (m, 4H), 3.86 (t, J=6.3 Hz, 2H), 3.73 (dd, J=9.6, 3.4 Hz, 1H), 3.66 (dd, J=10.1, 3.4 Hz, 1H), 2.18 (s, 6H), 2.14 (s, 3H), 2.09 (s, 3H), 2.08 (s, 3H), 2.07 (s, 3H).

S7) 3'-Azido-3'-deoxy-3-O-[(5,6-Difluoro-2-oxo-3-chromenyl)methyl]-1,1'-sulfanediyl-di-β-D-galactopyranoside NaOMe (1 M, 10 mL) was added to a stirred solution of S6 (525 mg, 0.63 mmol) in MeOH (15 mL) and CH$_2$Cl$_2$ (2 mL). After stirring o.n. the pH was adjusted to 7 by Dowex and concentrated. The residue was purified by column chromatography (CH$_2$Cl$_2$:MeOH 19:1→9:1) to give S7 (195 mg, 53%).

HRMS calcd for [C$_{22}$H$_{25}$F$_2$N$_3$O$_{11}$NaS]$^+$, 600.1076; found: 600.1079.

Example 4

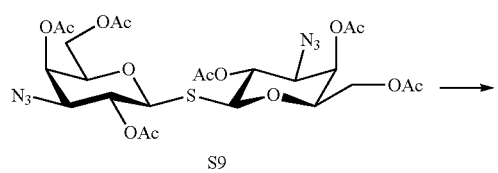

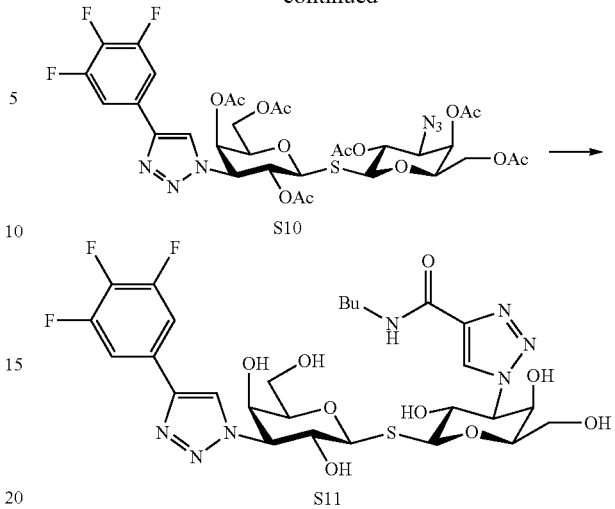

S11) 3-{4-[(Butylamino)carbonyl]-1H-1,2,3-triazol-1-yl}-3,3'-dideoxy-3'-[4-(3,4,5-trifluorophenyl)-1H-1,2,3-triazol-1-yl]-1,1'-sulfanediyl-di-β-D-galactopyranoside To a solution of S10 (26 mg, 0.032 mmol) and CuI (0.6 mg, 0.003 mmol) in DMF (3 mL) was methyl propiolate (0.004 mL, 0.048 mmol) added followed by diisopropylethylamine (0.005 mL, 0.032 mmol) and the mixture was stirred at 50° C. for 54 h. The reaction was quenched with sat. aq. NH$_4$Cl followed by evaporation of the solvent was evaporated and water was added. The mixture was extracted twice with CH$_2$Cl$_2$ and the organic phases were washed with brine, dried and evaporated. The obtained residue was stirred with a solution of butylamine 20% in MeOH for 3 days at rt. The solution was evaporated and the residue was purified with flash chromatography (CH$_2$Cl$_2$:MeOH 9:1) to give S11 (13.2 mg, 60%)

$^1$H-NMR (MeOD, 400 MHz) δ 8.59 (s, 1H), 8.55 (s, 1H), 7.43 (dd, J=8.8, 6.5 Hz, 2H,), 4.93 (dd, J=10.4, 2.9 Hz, 2H), 4.86 (d, J=9.5 Hz, 2H), 4.76 (m, 2H), 4.14 (d, J=2.7 Hz, 1H), 4.12 (d, J=2.7 Hz, 1H), 3.89-3.78 (m, 4H), 3.71 (m, 1H), 3.68 (m, 1H), 3.39 (t, J=7.0 Hz, 2H), 1.60 (m, 2H), 1.40 (m, 2H), 0.96 (t, J=7.3 Hz, 3H).

HRMS calcd for [C$_{27}$H$_{34}$F$_3$N$_7$O$_9$SNa]$^+$, 712.1980; found: 712.1989.

Preparation of Starting Material for Example 4

S10) 2,2',4,4',6,6'-Hexa-O-acetyl-3'-azido-3-3'-dideoxy-3-[4-(3,4,5-trifluorophenyl)-1H-1,2,3-triazol-1-yl]-1,1'-sulfanediyl-di-β-D-galactopyranoside To a solution of S9 (300 mg, 0.454 mmol) and CuI (8.6 mg, 0.045 mmol) in DMF (10 mL) was 3,4,5-trifluorophenylacetylene (0.042 mL, 0.409 mmol) added followed by diisopropylethylamine (0.079 mL, 0.454 mmol). The resulting suspension was stirred at rt for 1 h after which the reaction was quenched with sat. aq. NH$_4$Cl followed by evaporation of the solvent was evaporated and water was added. The mixture was extracted twice with CH$_2$Cl$_2$ and the organic phases were washed with brine, dried and evaporated. The obtained residue was purified with flash chromatography (heptane:EtOAc 1:1) to give S10 (90 mg, 24%).

¹H-NMR (CDCl₃, 400 MHz) δ 7.82 (s, 1H), 7.43 (t, J=8.0 Hz, 2H), 5.73 (t, J=10.4 Hz, 1H), 5.61 (d, J=2.7 Hz, 1H), 5.50 (d, J=2.5 Hz, 1H), 5.23 (t, J=10.0 Hz, 1H), 5.16 (dd, J=11.0, 3.2 Hz, 1H), 4.95 (d, J=9.7 Hz, 1H), 4.82 (d, J=10.0 Hz, 1H), 4.26-4.07 (m, 5H), 3.91 (t, J=6.4 Hz, 1H), 3.67 (dd, J=10.1, 3.3 Hz, 1H), 2.19 (s, 3H), 2.16 (s, 3H), 2.11 (s, 3H), 2.08 (s, 3H), 2.06 (s, 3H), 1.92 (s, 3H).

HRMS calcd for $[C_{32}H_{35}F_3N_6O_{14}SNa]^+$, 839.1782; found: 839.1771.

Example 5

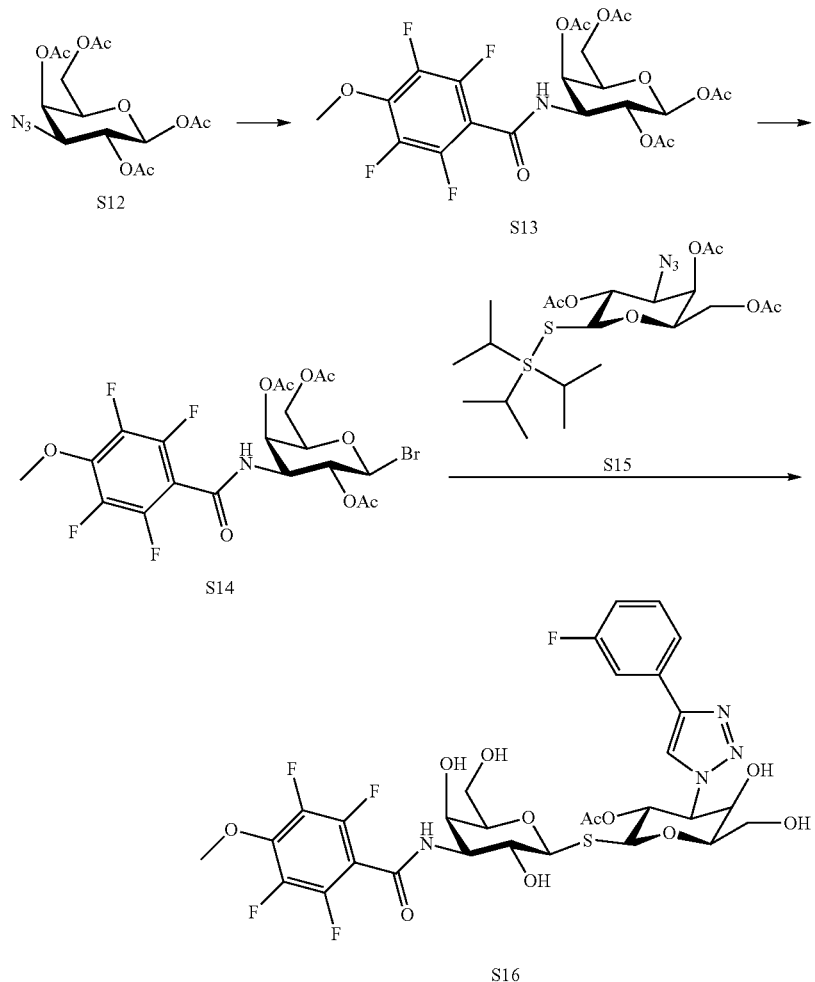

S16) 3,3'-Dideoxy-3'-[4-(3-fluorophenyl)-1H-1,2,3-triazol-1-yl]-3-(4-methoxy-2,3,5,6-tetrafluoro-benzamido)-1'-sulfanediyl-di-β-D-galactopyranoside S14 (22.5 mg, 0.036 mmol) and S15 (18.2 mg, 0.036 mmol) was dissolved in acetonitrile (10 ml) followed by addition of TBAF (11 μl, 1M). The reaction was stirred under nitrogen atmosphere for 1 hour followed by evaporation of the solvents. The crude material was dissolved in MeOH (10 ml) followed by addition of NaOMe (500 μl, 1M). The reaction mixture was stirred o.n. followed by adjustment of pH to neutral (pH7) using Duolit IR120, filtered, evaporation. The crude material was purified by flash chromatography (DCM/MeOH (8:1)) to give crude material. This material (12 mg, 0.020 mmol) was dissolved in DMF (8 ml) followed by addition of 1-ethynyl-3-fluorobensen (7 μl, 0.061 mmol), CuI (0.4 mg, 0.002 mmol) and triethylamine (2.8 μl, 0.020 mmol). The reaction was stirred under nitrogen atmosphere for 48 hour and followed by evaporation of the solvents. The crude material was purified by flash chromatography (DCM/MeOH (7:1)) to give the title compound S16 (6.2 mg, 24%).

¹H NMR (400 MHz, CD₃OD) δ 8.49 (s, 1H), 7.79-7.50 (m, 2H), 7.46 (td, J=8.0, 6.0 Hz, 1H), 7.08 (ddd, J=8.3, 2.6, 1.3 Hz, 1H), 5.26-4.76 (m, 3H), 4.52-4.28 (m, 1H), 4.18 (dd, J=10.4, 3.0 Hz, 1H), 4.12 (dd, J=3.7, 2.2 Hz, 4H), 4.04 (d, J=2.9 Hz, 1H), 3.90-3.64 (m, 7H).

ESIMS m/z calcd for $[C_{28}H_{30}F_5N4O_{10}S]^+$, 709.1603; found 709.1609.

Preparation of Starting Materials for Example 5

S13) 1,2,4,6-Tetra-O-acetyl-3-deoxy-3-(4-methoxy-2,3,5,6-tetrafluoro-benzamido)-β-D-galactopyranose Compound 1,2,4,6-tetra-O-acetyl-3-azido-3-deoxy-D-galactopyranose S12 (1600 mg, 4.286 mmol) was dissolved in ethanol (90 ml) and cyclohexene (180 ml). Palladium hydroxide (200 mg, 1.424 mmol) was added and the reaction was heated to reflux at 90° C. for 20 min. The reaction mixture was filtered, concentrated and dissolved in DCM (200 ml) and pyridine (1040 μl, 12.858 mmol) and 4-methoxy-2,3,5,6-tetrafluoro-benzoylchloride (1247 mg, 5.143 mmol) was added. The reaction was stirred for four hours under nitrogen atmosphere and then washed with NaHCO$_3$ (2*150 ml) and dried with MgSO$_4$. The residue was purified by flash chromatography (Heptane/EtOAc: 1:1) to give S13 (934 mg) in 40% yield.

$^1$H NMR (400 MHz, CDCl$_3$) δ 6.26 (d, J=7.3 Hz, 1H), 5.81 (dd, J=8.2, 3.1 Hz, 1H), 5.64-5.41 (m, 1H), 5.16 (ddd, J=11.2, 8.2, 3.0 Hz, 1H), 4.54 (td, J=7.8, 4.5 Hz, 1H), 4.23-3.96 (m, 6H), 2.28-1.93 (m, 12H).

ESIMS m/z calcd for [C$_{22}$H$_{23}$F$_4$NO$_{11}$Na]$^+$, 576.1105; found 576.1104.

S14) 2,4,6-Tri-O-acetyl-3-(4-methoxy-2,3,5,6-tetra-fluoro-benzamido)-α-D-galactopyranosyl bromide S13 (21.9 mg, 0.0395 mmol) was dissolved in DCM (4 ml) and Ac$_2$O (10.1 μl, 0.11 mmol) was added. The reaction mixture was stirred under nitrogen atmosphere and cooled to 0° C. HBr/AcOH (88 μl, 0.043 mmol) was added and the reaction was stirred for 2 hours, washed with NaHCO$_3$ (1*50 ml), brine (1*50 ml), dried over MgSO$_4$, filtered and concentrated to give S14 (20.1 mg) in 89% yield. $^1$H NMR (400 MHz, CDCl$_3$) δ 6.59 (d, J=3.8 Hz, 1H), 6.12 (d, J=7.9 Hz, 1H), 5.66 (dd, J=3.1, 1.1 Hz, 1H), 5.13 (dd, J=11.3, 3.8 Hz, 1H), 4.93 (ddd, J=11.2, 8.0, 3.1 Hz, 1H), 4.55 (t, J=6.4 Hz, 1H), 4.19 (dd, J=11.6, 6.0 Hz, 1H), 4.13 (t, J=1.7 Hz, 3H), 4.06 (dd, J=11.6, 6.9 Hz, 1H), 2.16 (s, 3H), 2.14 (s, 3H), 2.07 (s, 3H).

Examples 6 and 7

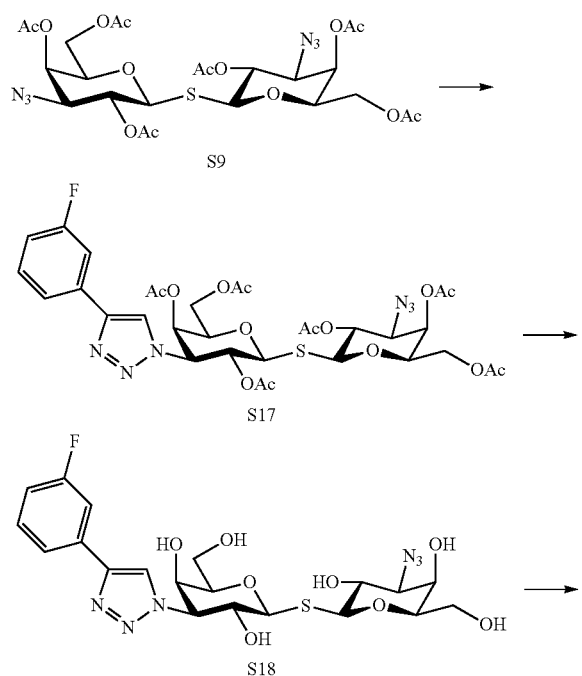

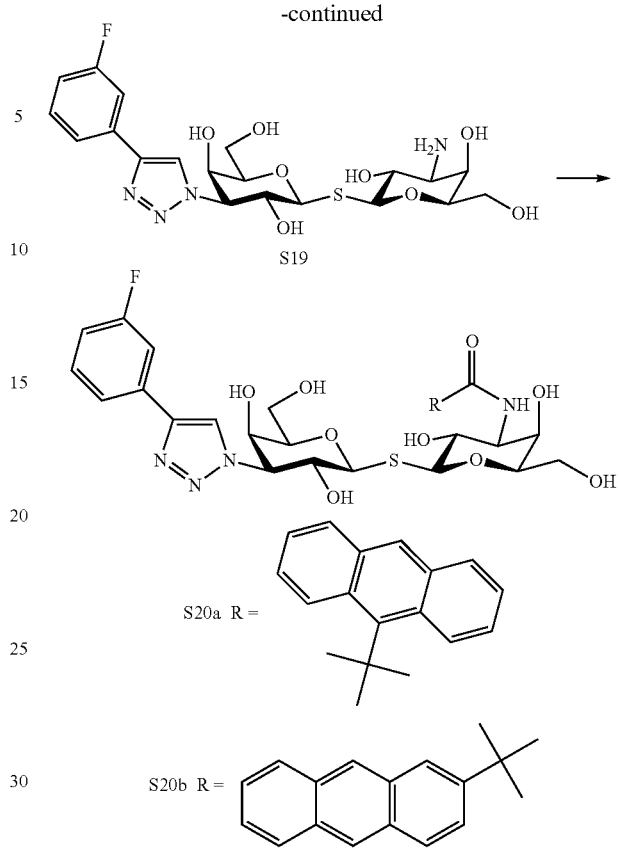

Example 6

S20a) 3-(9-anthracene carboxamide)-3,3'-Dideoxy-3-[4-(3-fluorophenyl)-1H-1,2,3-triazol-1-yl]-1,1'-sulfanediyl-di-β-D-galactopyranoside The amine compound S19 (37 mg, 0.07 mmol) was suspended in dry THF followed by addition of 9-Anthracene carbonyl chloride (35 mg, 0.14 mmol). The reaction mixture was stirred at room temperature under N$_2$ atmosphere. Et$_3$N (0.1 mL) was added. After 2 h 9-Anthracene carbonyl chloride (35 mg, 0.14 mmol) was added. The reaction was followed by TLC in 6:1 CH$_2$Cl$_2$:MeOH. After the reaction was complete, the solvents were evaporated and the residue was purified by flash chromatography using DCM:MeOH as eluent to afford pure compound 5 in 46% yield.

$^1$H NMR (CD$_3$OD, 400 MHz) δ: 8.58 (s, 1H), 8.50 (s, 1H), 8.39 (d, 9.2 Hz, 1H), 8.17 (d, 8.4 Hz, 1H), 8.08 (m, 2H), 7.66 (m, 7H), 7.10 (t, 1H), 4.94 (2H obscured under H$_2$O), 4.57 (m, 2H), 4.29 (d, 1H, 2.8 Hz), 4.12 (d, 1H, 2.4 Hz), 3.99 (t, 1H, 10.0 Hz), 3.87 (m, 7H).

$^{13}$C NMR (CD$_3$OD, 100 MHz) δ: 172.36, 165.88, 163.45, 134.36, 134.27, 133.26, 132.62, 131.93, 131.85, 129.53, 129.39, 129.16, 127.64, 126.96, 126.62, 126.34, 122.43, 115.88, 115.67, 113.31, 113.08, 86.85 (C-1), 86.53 (C-1'), 81.87, 81.44, 69.80, 69.74, 69.67, 68.98, 68.50, 63.03, 62.70, 58.47, 40.42.

HRMS m/z calcd. For C$_{35}$H$_{35}$N$_4$O$_9$FNaS (M+Na$^+$) 729.2000, found 729.2006.

Example 7

S20b) 3-(2-anthracene carboxamide)-3,3'-Dideoxy-3-[4-(3-fluorophenyl)-1H-1,2,3-triazol-1-yl]-1,1'-sulfanediyl-di-β-D-galactopyranoside The amine compound 4 (20 mg, 0.039 mmol) was suspended in dry THF followed by addition of 2-Anthracene carbonyl chloride (19.1 mg, 0.0796 mmol). The reaction mixture was stirred at room temperature under $N_2$ atmosphere. $Et_3N$ (0.1 mL) was added. After 2 h 2-Anthracene carbonyl chloride (19.1 mg, 0.0796 mmol) was added. The reaction was followed by TLC in 6:1 $CH_2Cl_2$:MeOH. After the reaction was complete, the solvents were evaporated and the residue was purified by flash chromatography using DCM:MeOH as eluent to afford pure compound 6 in 44% yield.

$^1$H NMR (CD$_3$OD, 400 MHz) δ: 8.66 (s, 1H, ArH), 8.62 (s, 1H, ArH), 8.53 (s, 2H, triazole-H, ArH), 8.13 (m, 3H, ArH), 7.92 (dd, 1.6 Hz and 1.6 Hz, 1H, ArH), 7.68 (m, 5H, ArH), 7.10 (m, 1H, ArH), 4.96 (3H obscured under H$_2$O, H-1, H-1', H-3), 4.53 (t, 10.4 Hz and 10.0 Hz, 1H, H-3), 4.29 (dd, 1H, H-3'), 4.16 (m, 3H, H-4, H-4', H-2'), 3.90 (m, 6H, H-5, H-5', H-6, H-6').

$^{13}$C NMR (CD$_3$OD, 100 MHz) δ: 134.32, 133.67, 132.53, 131.92, 129.88, 129.65, 129.36, 129.26, 129.07, 127.43, 127.25, 127.00, 124.37, 122.46, 113.31, 86.46, 86.43, 81.75, 81.44, 69.82, 69.43, 69.31, 69.01, 68.50, 63.06, 62.63, 58.95.

HRMS m/z calcd. For $C_{35}H_{35}N_4O_9FNaS$ (M+Na$^+$) 729.2000, found (M+Na) 729.2006.

Preparation of Starting Materials Examples 6 and 7

S17) 2,2',4,4',6,6'-Hexa-O-acetyl-3'-azido-3-3'-dideoxy-3-[4-(3-fluorophenyl)-1H-1,2,3-triazol-1-yl]-1,1'-sulfanediyl-di-β-D-galactopyranoside A solution of 2,2',4,4',6,6'-Hexa-O-acetyl-3,3'-diazido-3,3'-dideoxy-1,1'-sulfanediyl-di-β-D-galactoside (S9) (1.06 g, 1.60 mmol), 3-fluorophenyl acetylene (0.16 mL, 1.44 mmol), CuI (15.2 mg, 0.08 mmol) in dry $CH_3CN$ (20 mL) in a 100 mL round bottomed flask was stirred under nitrogen for 15 mins. $Et_3N$ (0.11 mL, 0.8 mmol) was added slowly via a syringe. The reaction mixture was stirred at room temperature for 1 h to afford monocycloaddition product, monitoring product formation using TLC 1:2, n-heptane-EtOAc. Solvents were evaporated in vacuo and the residue was dissolved in $CH_2Cl_2$ (40 mL) and washed successively with aqueous $NH_4Cl$ (20 mL) and brine (20 mL). The organic layer was separated, dried over $Na_2SO_4$ and the solvents were evaporated in vacuo. The residue was purified by flash chromatography using n-heptane-EtOAc as eluent to afford monotriazole S17 in 42% yield.

$^1$H NMR (CDCl$_3$, 400 MHz) δ: 7.83 (s, 1H), 7.54 (t, 2H, 7.6 Hz and 8.8 Hz), 7.38 (m, 1H), 7.03 (m, 1H), 5.73 (t, 1H, 10.4 Hz), 5.62 (d, 1H, 2.4 Hz), 5.50 (d, 1H, 2.4 Hz), 5.24 (m, 2H), 4.98 (d, 1H, 9.6 Hz), 4.85 (d, 1H, 10.0 Hz), 4.21 (m, 5H), 3.92 (m, 1H), 3.69 (dd, 1H, 10.4 Hz and 2.8 Hz).

S18) 3'-Azido-3,3'-dideoxy-3-[4-(3-fluorophenyl)-1H-1,2,3-triazol-1-yl]-1,1'-sulfanediyl-di-β-D-galactopyranoside The above monotriazole S17 (525 mg, 0.67 mmol) was treated with 0.5M NaOMe in MeOH until complete conversion monitored by TLC. The reaction mixture was neutralized using DOWEX H$^+$ resin. The resin was filtered off and the solvents where evaporated. The crude material was purified by flash chromatography using $CH_2Cl_2$:MeOH as eluent. This afforded compound S18 in 96% yield. $^1$H NMR (CD$_3$OD, 400 MHz) δ: 8.51 (s, 1H), 7.67 (dd, 1H), 7.61 (m, 1H), 7.46 (m, 1H), 7.07 (m, 1H), 4.93 (2H obscured under H$_2$O), 4.78 (d, 1H, 10.0 Hz), 4.48 (t, 1H, 10.0 Hz), 4.13 (d, 1H, 3.2 Hz), 4.04 (d, 1H, 9.6 Hz and 10.0 Hz), 3.97 (d, 1H, 2.4 Hz) 3.85 (m, 6H), 3.40 (dd, 1H, 9.6 Hz and 2.8 Hz 1H).

S19) 3'-Amino-3,3'-dideoxy-3-[4-(3-fluorophenyl)-1H-1,2,3-triazol-1-yl]-1,1'-sulfanediyl-di-β-D-galactopyranoside A solution of S18 (300 mg, 0.567 mmol) in MeOH (0.7 mL) and Pd/C (10%, 10 mg) was hydrogenated under a hydrogen atmosphere for 3 h at room temperature. The reaction was monitored by mass spectrometry. After the completion the reaction mixture was filtered through celite and the solvents were evaporated to give S19 in 86% yield. The material was used in the next step without further purification.

Example 8

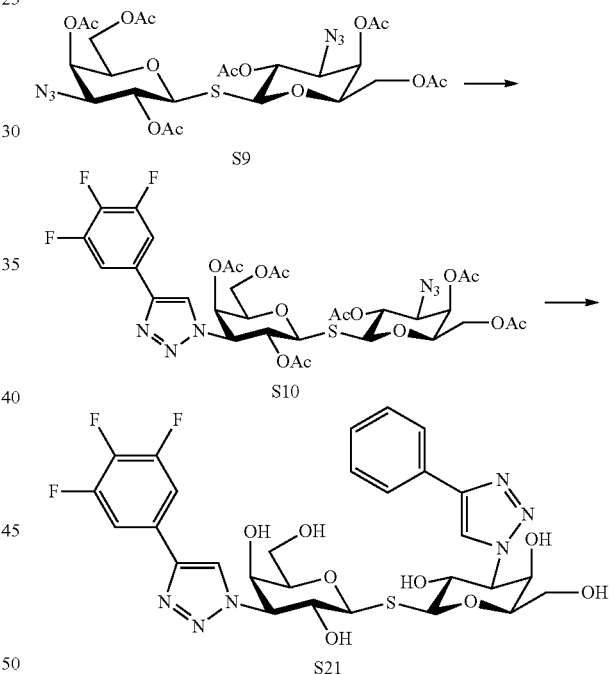

S21) 3,3'-Dideoxy-3-[4-(3,4,5-trifluorophenyl)-1H-1,2,3-triazol-1-yl]-3'-[4-phenyl-1H-1,2,3-triazol-1-yl]-1,1'-sulfanediyl-di-β-D-galactopyranoside S10 (50 mg), phenylacetylene (20 μl) and CuI (3 mg) were mixed and taken up in in acetonitrile (10 ml). The reaction mixture was degassed (argon) followed by addition of Hünig's base (50 μl). The reaction mixture was stirred at rt over night. The solvents were removed in vacuo followed by purification using flash chromatography (SiO2/heptane: ethyl acetate 95:5=>5:95). The appropriate fractions were combined and the solvents were removed in vacuo and the residue was dissolved in methanol (10 ml). 1M sodium methoxide in methanol (1.5 ml) was added and the reaction mixture was stirred for 2 h. TFA (0.2 ml) was added and the solvents were removed in vacuo. The residue was purified by HPLC (C18/MeCN:H$_2$O:0.1% TFA). Freezedrying afforded the title compound as a white solid (8 mg).

$^1$H NMR (400 MHz, Methanol-d$_4$) δ 8.59 (s, 1H), 8.52 (s, 1H), 7.82 (d, J=7.7 Hz, 2H), 7.65-7.56 (m, 2H), 7.42 (t, J=7.6 Hz, 2H), 7.33 (t, J=7.4 Hz, 1H), 4.85 (m, 6H), 4.16 (d, J=8.7 Hz, 2H), 3.91-3.78 (m, 4H), 3.72 (dd, J=11.2, 4.1 Hz, 2H).

ESI-MS m/z calcd for $[C_{28}H_{30}F_3N_6O_8S]^+$ (M+H)$^+$: 667.17; found: 667.1.

Preparation of Starting Material for Example 8

S10) 3'-Azido-3,3'-dideoxy-3-[4-(3,4,5-trifluorophenyl)-1H-1,2,3-triazol-1-yl]-1,1'-sulfanediyl-di-β-D-galactopyranoside 3,3'-Diazido-3,3'-dideoxy-1,1'-sulfanediyl-di-β-D-galactopyranoside S9 (131 mg) and trimethyl-[2-(3,4,5-trifluorophenyl)ethynyl]silane (45 μl) were dissolved in acetonitrile (5 ml), the reaction mixture was degassed (argon). Cesium fluoride (30 mg) was added and the reaction mixture was stirred for 5 min. CuI (4 mg) was added, followed by Hünig's base (100 μl). The mixture was stirred at rt over night followed by removal of solvents in vacuo. The residue was evaporated on to silica and purified by flash chromatography (SiO2/heptane:ethyl acetate 95:5=>5:95). The appropriate fractions were concentrated in vacuo and the residue dissolved in methanol (10 ml). 1M sodium methoxide in methanol (1.5 ml) was added and the reaction mixture was stirred for 2 h. TFA (0.2 ml) was added and the mixture concentrated in vacuo. The residue was purified by HPLC (C18/MeCN:H2O:0.1% TFA). Freezedrying afforded a white solid which was dissolved in pyridine (5 ml). Acetic anhydride (1 ml) was added and the reaction mixture was stirred at rt 5 h followed by removal of solvents in vacuo, the residue was dissolved in small amount of dichloromethane and filtered through a plug of silica. The solvent was removed in vacuo to afford S10 a white solid (84 mg).

$^1$H NMR (400 MHz, Methanol-d$_4$) δ 8.58 (d, J=1.2 Hz, 2H), 7.60 (dd, J=8.5, 6.5 Hz, 4H), 4.90 (d, J=3.3 Hz, 4H), 4.72 (t, J=10.1 Hz, 2H), 4.16 (d, J=2.8 Hz, 2H), 3.94-3.78 (m, 4H), 3.72 (dd, J=11.3, 4.4 Hz, 2H).

Experimental Section 2

Evaluation of Kd Values

The affinity of compounds 3a-c for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47 (Sörme et al., 2004) and Monovalent interactions of GAlectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al. 2010). The assay was adapted to be able to measure the high affinity of the present compound for galectin-3 by using a probe (SY) constructed to have high affinity for galectin-3 based on the structure of 3,3'-dideoxy-3,3'-di-[4-(3-fluorophenyl)-1H-1, 2,3-triazol-1-yl]-1,1'-sulfanediyl-di-β-D-galactopyranoside which made it possible to use a low concentration of galectin-3 (50 nM). 100 nM albumin was included as a carrier to prevent protein loss at such low concentration of galectin.

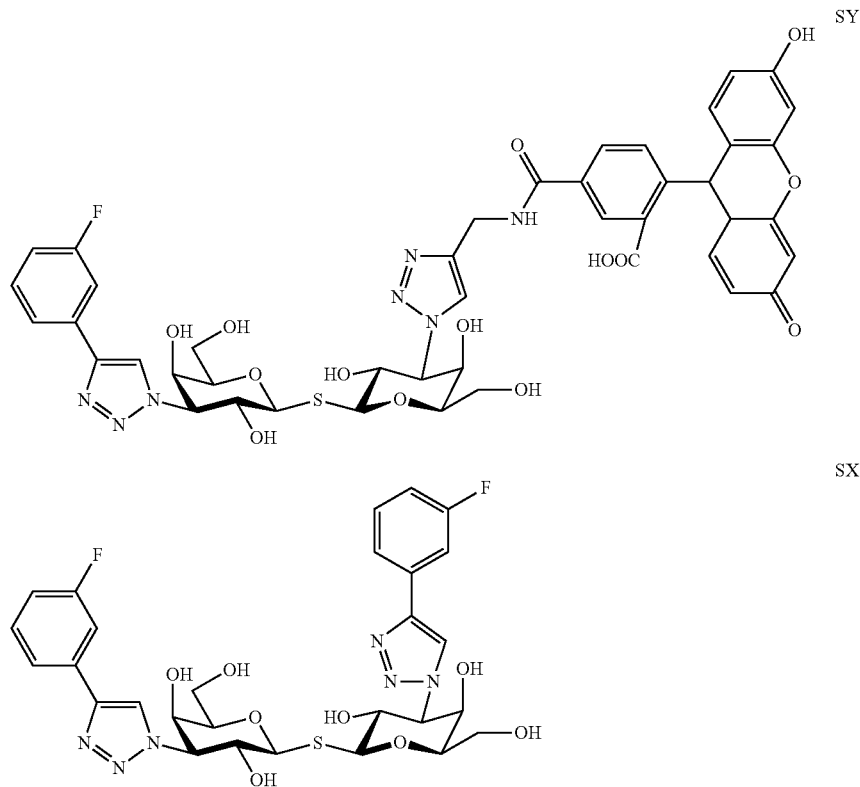

Kd values for compounds 3a-c and reference compound 3,3'-Dideoxy-3,3'-di-[4-(3-fluorophenyl)-1H-1,2,3-triazol-1-yl]-1,1'-sulfanediyl-di-β-D-galactopyranoside (SX)

| Example | Galectin-1 Kd (μM) | Galectin-3 Kd (μM) |
| --- | --- | --- |
| 3a | 0.078 | 0.003 |
| 3b | 0.079 | 0.001 |
| 3c | 0.110 | 0.002 |
| SX | 0.060 | 0.001 |

Materials and Methods

NMR spectra were recorded on a Bruker Avance II 400 MHz spectrometer at ambient temperature. $^1$H-NMR spectra were assigned using 2D-methods (COSY). Chemical shifts are given in ppm downfield from the signal for Me$_4$Si, with reference to residual CHCl$_3$ or CD$_2$HOD. HRMS was recorded on a Micromass Q-TOF micro spectrometer (ESI). Reactions were monitored by TLC using aluminum-backed silica gel plates (Merck 60F$_{254}$) and visualized using UV light and by chaffing with ethanolic H$_2$SO$_4$ (7%). Column chromatography was performed using silica gel (40-60 μm, 60 Å). Solvents were dried by storing over activated M.S. Reagents were supplied by Sigma-Aldrich and used as it is.

Synthesis

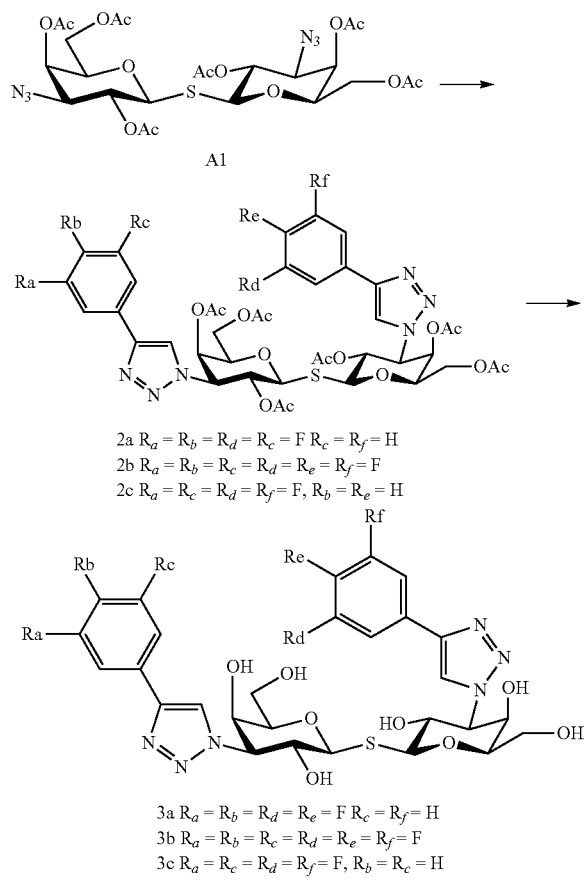

Experimental Procedures

Example 1.1

2,2',4,4',6,6'-Hexa-O-acetyl-3,3'-dideoxy-3,3'-di-[4-(3,4-difluorophenyl)-1H-1,2,3-triazol-1-yl]-1,1'-sulfanediyl-di-β-D-galactopyranoside 2a To a mixture of A1 (300 mg, 0.45 mmol) (van Scherpenzeel, M.; Moret, E. E.; Ballell, L.; Liskamp, R. M. J.; Nilsson, U. J.; Leffler, H.; Pieters, R. J. Synthesis and Evaluation of New Thiodigalactoside-Based Chemical Probes to Label Galectin-3. ChemBioChem 2009, 10, 1724-1733) and CuI (17 mg, 0.091 mmol) in acetonitrile (30 mL) was 3,4-difluorophenylacetylene (0.14 mL, 1.14 mmol) added followed by diisopropylethylamine (0.079 mL, 0.45 mmol). The resulting mixture was stirred at 50° C. for 8 h. The reaction was quenched with sat. aq. NH$_4$Cl and the solvent was evaporated. Water was added to the residue and extracted twice with CH$_2$Cl$_2$; the organic phases were washed with brine, dried and evaporated. The obtained residue was purified by column chromatography (heptane:EtOAc 1:1→1:4) to give 2a (115 mg, 23%).

$^1$H-NMR (CDCl$_3$, 400 MHz) δ 7.98 (s, 2H), 7.73 (td, J=9.5, 2.1 Hz, 2H), 7.60 (m, 2H), 7.21 (t, J=7.6 Hz, 2H), 5.88 (t, J=9.7 Hz, 2H), 5.62 (d, J=2.3 Hz, 2H), 5.16 (dd, J=11.1, 3.1 Hz, 2H), 4.89 (d, J=9.6 Hz, 2H), 4.55 (dd, J=11.6, 7.0 Hz, 2H), 4.20 (t, J=6.6 Hz, 2H), 4.05 (dd, J=11.7, 5.0 Hz, 2H), 2.15 (s, 6H), 2.13 (s, 6H), 1.92 (s, 6H).

Example 2.1

2,2',4,4',6,6'-Hexa-O-acetyl-3,3'-bisdeoxy-3,3'-bis-[4-(3,4,5-trifluorophenyl)-1H-1,2,3-triazol-1-yl]-1,1'-sulfanediyl-di-β-D-galactopyranoside 2b To a mixture of A1 (300 mg, 0.45 mmol) and CuI (17 mg, 0.091 mmol) in acetonitrile (20 mL) was 3,4,5-trifluorophenylacetylene (0.086 mL, 0.72 mmol) added followed by diisopropylethylamine (0.079 mL, 0.45 mmol). The resulting mixture was stirred at 50° C. for 6 h. The reaction was quenched with sat. aq. NH$_4$Cl and the solvent was evaporated. Water was added to the residue and extracted twice with CH$_2$Cl$_2$; the organic phases were washed with brine, dried and evaporated. The obtained residue was purified by column chromatography (heptane:EtOAc 1:1→1:4) to give 2b (28 mg, 6%).

$^1$H-NMR (CDCl$_3$, 400 MHz) δ 8.12 (s, 2H), 7.60 (dd, J=8.3, 6.4 Hz, 4H), 5.95 (dd, J=11.0 9.5 Hz, 2H), 5.62 (d, J=2.7 Hz, 2H), 5.13 (dd, J=11.0, 3.3 Hz, 2H), 4.81 (d, J=9.5 Hz, 2H), 4.74 (dd, J=12.6, 7.4 Hz, 2H), 4.23 (m, 2H), 3.98 (dd, J=11.7, 4.1 Hz, 2H), 2.20 (s, 6H), 2.15 (s, 6H), 1.92 (s, 6H).

Example 3.1

2,2',4,4',6,6'-Hexa-O-acetyl-3,3'-bisdeoxy-3,3'-bis-[4-(3,5-difluorophenyl)-1H-1,2,3-triazol-1-yl]-1,1'-sulfanediyl-di-β-D-galactopyranoside 2c To a mixture of A1 (505 mg, 0.76 mmol) and CuI (77 mg, 0.40 mmol) in acetonitrile (30 mL) was 3,5-difluorophenylacetylene (0.224 mL, 1.89 mmol) added followed by diisopropylethylamine (0.132 mL, 0.76 mmol). The resulting mixture was stirred at r.t. for 2 h. The reaction was quenched with brine and the mixture was extracted with Et$_2$O. The organic phase was washed once with brine and the combined water phases extracted once with Et$_2$O. The combined organic phases were dried (Na$_2$SO$_4$) and evaporated. The obtained residue 2c was used without further purification in next step.

ESI-MS m/z calcd for [C$_{40}$H$_{41}$F$_4$N$_6$O$_{14}$S]$^+$, (M+H)$^+$, 937.2; found: 937.2.

Example 4.1

3,3'-dideoxy-3,3'-di-[4-(3,4-difluorophenyl)-1H-1,2,3-triazol-1-yl]-1,1'-sulfanediyl-di-β-D-galactopyranoside 3a NaOMe (1 M, 3 mL) was added to a stirred solution of 2a (115 mg, 0.12 mmol) in MeOH (12 mL) and CH$_2$Cl$_2$ (3 mL). After 18 hours was the solution adjusted to pH 7 by Dowex and concentrated. The residue was purified by column chromatography (CH$_2$Cl$_2$:MeOH 19:1→4:1) to give 3a (36 mg, 43%).

$^1$H-NMR (MeOD, 400 MHz) δ 8.55 (s, 2H), 7.72 (ddd, J=11.5, 7.6, 2.1 Hz, 2H), 7.60 (m, 2H), 7.30 (td, J=10.4, 7.6 Hz, 2H), 4.92 (obscured by water, 4H), 4.77 (t, J=9.8 Hz, 2H), 4.16 (d, J=2.6 Hz, 2H), 3.90 (m, 2H), 3.83 (m, 2H), 3.72 (dd, J=11.5, 4.4 Hz, 2H).

HRMS calcd for [C$_{28}$H$_{29}$N$_6$O$_8$F$_4$S]$^+$, 685.1704; found: 685.1696.

Example 5.1

3,3'-bisdeoxy-3,3'-bis-[4-(3,4,5-trifluorophenyl)-1H-1,2,3-triazol-1-yl]-1,1'-sulfanediyl-di-β-D-galactopyranoside 3b NaOMe (1 M, 2 mL) was added to a stirred solution of 2b (28 mg, 0.029 mmol) in MeOH (4 mL) and CH$_2$Cl$_2$ (1 mL). After 3 days was the solution adjusted to pH 7 by Dowex and concentrated. The residue was purified by column chromatography (CH$_2$Cl$_2$:MeOH 19:1→9:1) to give 3b (14 mg, 68%).

$^1$H-NMR (MeOD, 400 MHz) δ 8.59 (s, 2H), 7.60 (dd, J=8.7, 6.6 Hz, 4H), 4.92 (obscured by water, 4H), 4.72 (t, J=9.7 Hz, 2H), 4.16 (d, J=2.7 Hz, 2H), 3.90 (m, 2H), 3.83 (m, 2H), 3.72 (dd, J=11.4, 4.4 Hz, 2H).

HRMS calcd for [C$_{28}$H$_{27}$N$_6$O$_8$F$_6$S]$^+$, 721.1515; found: 721.1514.

Example 6.1

3,3'-bisdeoxy-3,3'-bis-[4-(3,5-difluorophenyl)-1H-1,2,3-triazol-1-yl]-1,1'-sulfanediyl-di-β-D-galactopyranoside 3c NaOMe (183 mg, 3.39 mmol) was added to a stirred solution of 2c (0.76 mmol, crude from previous step) in MeOH (40 mL) and CH$_2$Cl$_2$ (10 mL). After 18 hours was the solution adjusted to pH 7 by AcOH and concentrated. The residue was purified by column chromatography (EtOAc:MeOH 10:1) and re-crystalized from MeCN to give 3c in 27% yield over two steps.

$^1$H NMR (400 MHz, DMSO-d$_6$) δ 8.77 (s, 2H), 7.65-7.56 (m, 4H), 7.19 (tt, J=9.4, 2.5 Hz, 2H), 5.38 (dd, J=6.8, 2.0 Hz, 4H), 4.94 (d, J=9.5 Hz, 2H), 4.87 (dd, J=10.6, 3.0 Hz, 2H), 4.71 (t, J=5.7 Hz, 2H), 4.15-4.26 (m, 2H), 3.98 (dd, J=6.6, 3.0 Hz, 2H), 3.74 (t, J=6.3 Hz, 2H), 3.47-3-63 (m, 4H).

ESI-MS m/z calcd for [C$_{28}$H$_{29}$N$_6$O$_8$F$_4$S]$^+$, (M+H)$^+$, 685.2; found: 685.0.

REFERENCES

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. Infect. Immun. Vol. 69: 832-837.

Barondes, S. H., Cooper, D. N. W., Gitt, M. A., and Leffler, H. (1994). Galectins. Structure and function of a large family of animal lectins. J. Biol. Chem. 269:20807-20810.

Blois, S. M., Ilarregui, J. M., Tometten, M., Garcia, M., Orsal, A. S., Cordo-Russo, R., Toscano, M. A., Bianco, G. A., Kobelt, P., Handjiski, B., et al. (2007). A pivotal role for galectin-1 in fetomaternal tolerance. Nat Med 13: 1450-1457.

Chen, W.-S., Leffler H., Nilsson, U. J., Panjwani, N. (2012). Targeting Galectin-1 and Galectin-3 Attenuates VEGF-A-induced Angiogenesis; Mol. Biol. Cell (suppl), Abstract No. 2695.

Cumpstey, I., Carlsson, S., Leffler, H. and Nilsson, U. J. (2005) Synthesis of a phenyl thio-β-D-galactopyranoside library from 1,5-difluoro-2,4-dinitrobenzene: discovery of efficient and selective monosaccharide inhibitors of galectin-7. Org. Biomol. Chem. 3: 1922-1932.

Cumpstey, I., Sundin, A., Leffler, H. and Nilsson, U. J. (2005) C$_2$-Symmetrical thiodigalactoside bis-benzamido derivatives as high-affinity inhibitors of galectin-3: Efficient lectin inhibition through double arginine-arene interactions. Angew. Chem. Int. Ed. 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. Chem. Eur. J. 14: 4233-4245.

Dam, T. K., and Brewer, C. F. (2008). Effects of clustered epitopes in multivalent ligand-receptor interactions. Biochemistry 47: 8470-8476.

Delacour, D., Greb, C., Koch, A., Salomonsson, E., Leffler, H., Le Bivic, A., and Jacob, R. (2007). Apical Sorting by Galectin-3-Dependent Glycoprotein Clustering. Traffic 8: 379-388.

Delaine, T., Cumpstey, I., Ingrassia, L., Le Mercier, M., Okechukwu, P., Leffler, H., Kiss, R., and Nilsson, U. J. (2008). Galectin-Inhibitory Thiodigalactoside Ester Derivatives Have Anti-Migratory Effects in Cultured Lung and Prostate Cancer Cells. J Med Chem 51; 8109-8114.

Garner, O. B., and Baum, L. G. (2008). Galectin-glycan lattices regulate cell-surface glycoprotein organization and signalling. Biochem Soc Trans 36: 1472-1477.

Giguere, D., Patnam, R., Bellefleur, M.-A., St.-Pierre, C., Sato, S., and Roy, R. (2006). Carbohydrate triazoles and isoxazoles as inhibitors of galectins-1 and -3. Chem Commun: 2379-2381.

Glinsky, G. V., Price, J. E., Glinsky, V. V., Mossine, V. V., Kiriakova, G., and Metcalf, J. B. (1996). Cancer Res 56: 5319-5324.

Glinsky, V. V., Kiriakova, G., Glinskii, O. V., Mossine, V. V., Mawhinney, T. P., Turk, J. R., Glinskii, A. B., Huxley, V. H., Price, J. E., and Glinsky, G. V. (2009). Synthetic Galectin-3 Inhibitor Increases Metastatic Cancer Cell Sensitivity to Taxol-Induced Apoptosis In Vitro and In Vivo. Neoplasia 11; 901-909.

Huflejt, M. E. and Leffler, H. (2004) Galectin-4 in normal tissues and cancer. Glycoconj. J. 20: 247-255.

Ingrassia et al. (2006) A Lactosylated Steroid Contributes in Vivo Therapeutic Benefits in Experimental Models of Mouse Lymphoma and Human Glioblastoma. *J. Med. CHem.* 49: 1800-1807.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast Cancer. *Clin. Cancer Res.* 9: 2374-2383.

Lau, K. S., and Dennis, J. W. (2008). N-Glycans in cancer progression. *Glycobiology* 18: 750-760.

Lau, K. S., Partridge, E. A., Grigorian, A., Silvescu, C. I., Reinhold, V. N., Demetriou, M., and Dennis, J. W. (2007). Complex N-glycan number and degree of branching cooperate to regulate cell proliferation and differentiation. *Cell* 129: 123-134.

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Lin, C.-I., Whang, E. E., Donner, D. B., Jiang, X., Price, B. D., Carothers, A. M., Delaine, T., Leffler, H., Nilsson, U. J., Nose, V., et al. (2009). Galectin-3 Targeted Therapy with a Small Molecule Inhibitor Activates Apoptosis and Enhances Both Chemosensitivity and Radiosensitivity in Papillary Thyroid Cancer. *Mol Cancer Res* 7: 1655-1662.

MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. *J. Immun.* 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. *Am. J. Resp. Crit. Care Med.*, in press.

Massa, S. M., Cooper, D. N. W., Leffler, H., Barondes, S. H. (1993) L-29, an endogenous lectin, binds to glycoconjugate ligands with positive cooperativity. *Biochemistry* 32: 260-267.

Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. *Science* 306: 120-124.

Perone, M. J., Bertera, S., Shufesky, W. J., Divito, S. J., Montecalvo, A., Mathers, A. R., Larregina, A. T., Pang, M., Seth, N., Wucherpfennig, K. W., et al. (2009). Suppression of autoimmune diabetes by soluble galectin-1. *J Immunol* 182: 2641-2653.

Pienta, K. J., Naik, H., Akhtar, A., Yamazaki, K., Reploge, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Saegusa, J., Hsu, D. K., Chen, H. Y., Yu, L., Fermin, A., Fung, M. A., and Liu, F. T. (2009). Galectin-3 is critical for the development of the allergic inflammatory response in a mouse model of atopic dermatitis. *Am J Pathol* 174: 922-931.

Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejler, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Sörme, P., Qian, Y., Nyholm, P.-G., Leffler, H., Nilsson, U. J. (2002) Low micromolar inhibitors of galectin-3 based on 3'-derivatization ofN-acetyllactosamine. *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., Magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Thijssen, V. L., Poirer, F., Baum, L. G., and Griffioen, A. W. (2007). Galectins in the tumor endothelium: opportunities for combined cancer therapy. *Blood* 110: 2819-2827.

Toscano, M. A., Bianco, G. A., Ilarregui, J. M., Croci, D. O., Correale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8: 825-834.

We claim:

1. A compound of formula (1)

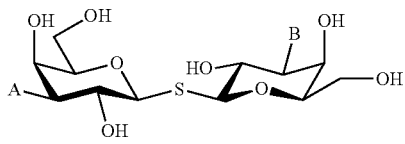

Wherein
A is

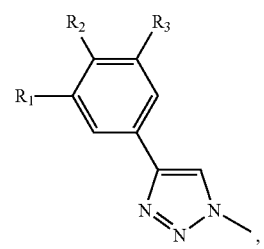

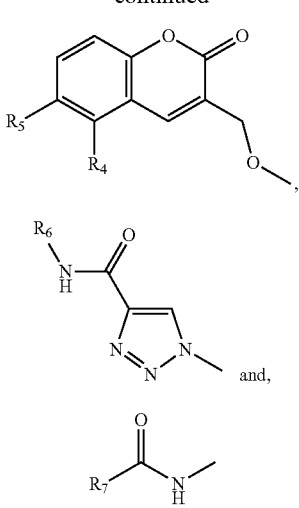

wherein R₁-R₃ are independently selected from hydrogen (H), fluorine, methyl optionally substituted with a fluorine (F), and OCH₃ optionally substituted with a F; and B is selected from

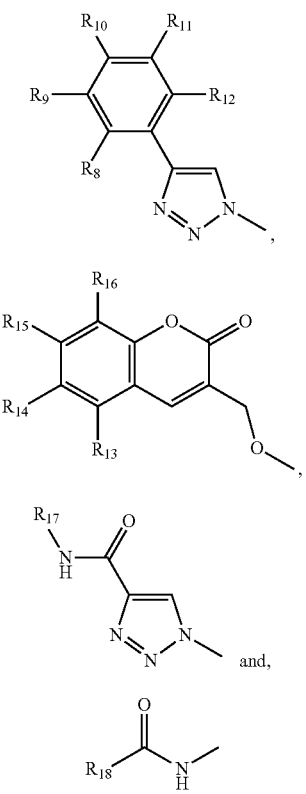

wherein $R_{13}$-$R_{16}$ are independently selected from H, F, methyl optionally substituted with a F, and OCH₃ optionally substituted with a F;

$R_{17}$ is selected from $C_{1-6}$ alkyl, branched $C_{3-6}$ alkyl and $C_{3-7}$ cycloalkyl;

$R_{18}$ is selected from aryl optionally substituted with a F, Cl, methyl optionally substituted with a F, and OCH₃ optionally substituted with a F; or a pharmaceutically acceptable salt or solvate thereof.

2. The compound of claim 1 wherein A is selected from formula 2 and B is selected from formula 7.

3. The compound of claim 2 wherein $R_1$-$R_3$ are independently selected from H or F, and wherein $R_{13}$-$R_{14}$ are both F, and $R_{15}$-$R_{16}$ are both H.

4. The compound of claim 3 wherein $R_1$ is H, $R_2$ is H, and $R_3$ is F.

5. The compound of claim 3 wherein $R_1$-$R_3$ are F.

6. The compound of claim 1 wherein A is selected from formula 2 and B is selected from formula 8.

7. The compound of claim 6 wherein $R_1$-$R_3$ are independently selected from H or F, and $R_{17}$ is $C_{1-5}$ alkyl.

8. The compound of claim 6 wherein $R_1$-$R_3$ are all F, and $R_{17}$ is tert-butyl or n-butyl.

9. The compound of claim 1 wherein A is selected from formula 2 and B is selected from formula 9.

10. The compound of claim 9 wherein $R_1$-$R_3$ are independently selected from H or F, and $R_{18}$ is selected from phenyl substituted with four F and one OCH₃, such as 2,3,5,6-tetrafluoro-4-methoxy-phenyl; 2-anthracenyl; 9-anthracenyl; 1-Naphtyl and 2-Naphtyl.

11. The compound of claim 9 wherein $R_1$-$R_3$ are all F, and $R_{18}$ is selected from 2,3,5,6-tetrafluoro-4 methoxy-phenyl.

12. The compound of claim 1 which is selected from
3'-Deoxy-3-O-[(5,6-difluoro-2-oxo-3-chromenyl)methyl]-3'-[4-(3-fluorophenyl)-1H-1,2,3-triazol-1-yl]-1,1'-sulfanediyl-di-β-D-galactopyranoside,
3'-Deoxy-3-O-[(5,6-difluoro-2-oxo-3-chromenyl)methyl]-3'-[4-(3,4,5-trifluorophenyl)-1H-1,2,3-triazol-1-yl]-1,1'-sulfanediyl-di-β-D-galactopyranoside,
3-{4-[(Butylamino)carbonyl]-1H-1,2,3-triazol-1-yl}-3,3'-dideoxy-3'-[4-(3,4,5-trifluorophenyl)-1H-1,2,3-triazol-1-yl]-1,1'-sulfanediyl-di-β-D-galactopyranoside,
3,3'-Dideoxy-3'-[4-(3-fluorophenyl)-1H-1,2,3-triazol-1-yl]-3-(4-methoxy-2,3,5,6-tetrafluoro-benzamido)-1,1'-sulfanediyl-di-β-D-galactopyranoside,
3-(9-anthracene carboxamide)-3,3'-Dideoxy-3-[4-(3-fluorophenyl)-1H-1,2,3-triazol-1-yl]-1,1'-sulfanediyl-di-β-D-galactopyranoside and
3-(2-anthracene carboxamide)-3,3'-Dideoxy-3-[4-(3-fluorophenyl)-1H-1,2,3-triazol-1-yl]-1,1'-sulfanediyl-di-β-D-galactopyranoside.

13. A composition comprising the compound of claim 1 and a pharmaceutically acceptable additive.

14. The composition according to claim 13, wherein said pharmaceutically active additive is a carrier or excipient.

15. A method for treatment of a disorder relating to the binding of a galectin, to a ligand in a mammal, wherein a therapeutically effective amount of at least one compound according to claim 1 is administered to a mammal in need of said treatment, wherein said disorder is selected from the group consisting of inflammation, fibrosis, septic shock, cancer, autoimmune diseases, metabolic disorders, heart disease, heart failure, pathological angiogenesis, and eye diseases.

16. The method according to claim 15, wherein said mammal is a human subject.

17. The method according to claim 15, wherein said galectin is galectin-3.

18. The method according to claim 15, wherein said fibrosis is pulmonary fibrosis or a solid organ fibrosis.

19. The method according to claim 18, wherein said solid organ fibrosis is selected from the group consisting of liver fibrosis, kidney fibrosis, ophthalmological fibrosis and fibrosis of the heart.

20. The method according to claim 15, wherein said angiogenesis is ocular angiogenesis or a disease or condition associated with ocular angiogenesis.

21. The method according to claim 20, where said disease or condition associated with ocular angiogenesis is neovascularization related to cancer.

22. The method according to claim 15, wherein said eye disease is selected from the group consisting of age-related macular degeneration and corneal neovascularization.

* * * * *